US009475792B2

(12) United States Patent
Parham et al.

(10) Patent No.: US 9,475,792 B2
(45) Date of Patent: Oct. 25, 2016

(54) MATERIALS FOR ORGANIC ELECTROLUMINESCENCE DEVICES

(75) Inventors: Amir Hossain Parham, Frankfurt (DE); Christof Pflumm, Frankfurt (DE); Arne Buesing, Frankfurt (DE); Holger Heil, Frankfurt am Main (DE); Philipp Stoessel, Frankfurt (DE)

(73) Assignee: Merck Patent GmbH (DE)

( * ) Notice: Subject to any disclaimer, the term of this patent is extended or adjusted under 35 U.S.C. 154(b) by 1095 days.

(21) Appl. No.: 13/144,841

(22) PCT Filed: Dec. 22, 2009

(86) PCT No.: PCT/EP2009/009220

§ 371 (c)(1),
(2), (4) Date: Jul. 15, 2011

(87) PCT Pub. No.: WO2010/083872

PCT Pub. Date: Jul. 29, 2010

(65) Prior Publication Data

US 2011/0272684 A1 Nov. 10, 2011

(30) Foreign Application Priority Data

Jan. 20, 2009 (DE) ........................ 10 2009 005 289

(51) Int. Cl.

| | |
|---|---|
| ***H01L 51/54*** | (2006.01) |
| ***C07D 213/89*** | (2006.01) |
| ***C07C 321/26*** | (2006.01) |
| ***C07C 13/573*** | (2006.01) |
| ***C07D 333/52*** | (2006.01) |
| ***C07D 487/04*** | (2006.01) |
| ***C07C 211/54*** | (2006.01) |
| ***C07D 487/14*** | (2006.01) |
| ***C07D 333/76*** | (2006.01) |
| ***C07D 209/94*** | (2006.01) |
| ***C07D 333/50*** | (2006.01) |
| ***C07D 333/78*** | (2006.01) |
| ***C07D 401/04*** | (2006.01) |
| ***C07D 401/14*** | (2006.01) |
| ***C07D 403/04*** | (2006.01) |
| ***C07D 403/14*** | (2006.01) |
| ***C07D 409/04*** | (2006.01) |
| ***C07D 409/14*** | (2006.01) |
| ***C07D 413/04*** | (2006.01) |
| ***C07D 413/14*** | (2006.01) |
| ***C07D 495/04*** | (2006.01) |
| ***C07F 9/6553*** | (2006.01) |
| ***C09K 11/06*** | (2006.01) |
| ***H01L 51/00*** | (2006.01) |
| ***H05B 33/14*** | (2006.01) |
| ***C09B 15/00*** | (2006.01) |
| ***C09B 17/00*** | (2006.01) |
| ***C09B 19/00*** | (2006.01) |
| ***C09B 57/00*** | (2006.01) |
| *H01L 51/50* | (2006.01) |

(52) U.S. Cl.
CPC ........... *C07D 333/76* (2013.01); *C07D 209/94* (2013.01); *C07D 333/50* (2013.01); *C07D 333/78* (2013.01); *C07D 401/04* (2013.01); *C07D 401/14* (2013.01); *C07D 403/04* (2013.01); *C07D 403/14* (2013.01); *C07D 409/04* (2013.01); *C07D 409/14* (2013.01); *C07D 413/04* (2013.01); *C07D 413/14* (2013.01); *C07D 487/04* (2013.01); *C07D 495/04* (2013.01); *C07F 9/655354* (2013.01); *C09B 15/00* (2013.01); *C09B 17/00* (2013.01); *C09B 19/00* (2013.01); *C09B 57/00* (2013.01); *C09B 57/008* (2013.01); *C09K 11/06* (2013.01); *H01L 51/0059* (2013.01); *H01L 51/0072* (2013.01); *H01L 51/0074* (2013.01); *H05B 33/14* (2013.01); *C09K 2211/1011* (2013.01); *C09K 2211/1014* (2013.01); *C09K 2211/1029* (2013.01); *C09K 2211/1033* (2013.01); *C09K 2211/1092* (2013.01); *H01L 51/5012* (2013.01); *H01L 51/5016* (2013.01); *H01L 51/5048* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 4,539,507 | A | 9/1985 | VanSlyke et al. |
| 5,151,629 | A | 9/1992 | VanSlyke |
| 5,621,131 | A | 4/1997 | Kreuder et al. |
| 5,840,217 | A | 11/1998 | Lupo et al. |
| 6,169,163 | B1 | 1/2001 | Woo et al. |
| 6,458,909 | B1 | 10/2002 | Spreitzer et al. |

(Continued)

FOREIGN PATENT DOCUMENTS

| | | | |
|---|---|---|---|
| CN | 101228250 | A | 7/2008 |
| CN | 102056889 | A | 5/2011 |

(Continued)

OTHER PUBLICATIONS

Zhao et al., "Effect of Substituents on the Properties of Indolo[3,2-*b*]Carbazole-Based hole-Transporting Materials", *Organic Electronics*, vol. 8, pp. 673-682 (2007).

*Primary Examiner* — J. L. Yang
(74) *Attorney, Agent, or Firm* — Drinker Biddle & Reath LLP

(57) ABSTRACT

The present invention describes indenofluorene derivatives of the general formula I, II, III or IV having emitting and hole-transporting properties, in particular for use in the emission and/or charge-transport layer of electroluminescent devices. The invention furthermore relates to a process for the preparation of the compounds according to the invention and to electronic devices comprising same.

9 Claims, No Drawings

(56) References Cited

U.S. PATENT DOCUMENTS

| | | | |
|---|---|---|---|
| 6,653,438 B1 | 11/2003 | Spreitzer et al. | |
| 2002/0158242 A1 | 10/2002 | Son et al. | |
| 2005/0040390 A1 | 2/2005 | Pfeiffer et al. | |
| 2005/0121667 A1 | 6/2005 | Kuehl et al. | |
| 2006/0063027 A1 | 3/2006 | Vestweber et al. | |
| 2006/0125009 A1 | 6/2006 | Wu et al. | |
| 2006/0175958 A1 | 8/2006 | Gerhard et al. | |
| 2006/0284140 A1 | 12/2006 | Breuning et al. | |
| 2007/0060736 A1 | 3/2007 | Becker et al. | |
| 2007/0170419 A1 | 7/2007 | Gerhard et al. | |
| 2007/0205714 A1 | 9/2007 | Busing et al. | |
| 2008/0220285 A1* | 9/2008 | Vestweber et al. | 428/690 |
| 2009/0066225 A1* | 3/2009 | Kimura et al. | 313/504 |
| 2009/0072712 A1 | 3/2009 | Stoessel et al. | |
| 2009/0134384 A1 | 5/2009 | Stoessel et al. | |
| 2009/0184313 A1 | 7/2009 | Buesing et al. | |
| 2009/0261717 A1 | 10/2009 | Buesing et al. | |
| 2010/0012931 A1* | 1/2010 | Kato et al. | 257/40 |
| 2010/0102305 A1 | 4/2010 | Heun et al. | |
| 2010/0187505 A1 | 7/2010 | Stoessel et al. | |
| 2010/0187977 A1 | 7/2010 | Kai et al. | |
| 2010/0227978 A1 | 9/2010 | Stoessel et al. | |
| 2011/0062429 A1 | 3/2011 | Kai et al. | |
| 2011/0068304 A1 | 3/2011 | Parham et al. | |

FOREIGN PATENT DOCUMENTS

| | | | | |
|---|---|---|---|---|
| DE | 102006025846 A1 | 12/2007 | | |
| EP | 0 676 461 A2 | 10/1995 | | |
| EP | 0 707 020 A2 | 4/1996 | | |
| EP | 0 842 208 A1 | 5/1998 | | |
| EP | 0 894 107 A1 | 2/1999 | | |
| EP | 1 028 136 A2 | 8/2000 | | |
| EP | 1175470 A1 | 1/2002 | | |
| EP | 1476881 A2 | 11/2004 | | |
| EP | 1596445 A1 | 11/2005 | | |
| EP | 1 655 359 A1 | 5/2006 | | |
| EP | 1860097 A1 | 11/2007 | | |
| EP | 2080762 A1 | 7/2009 | | |
| JP | 2003212875 A | 7/2003 | | |
| JP | 2003238516 A | 8/2003 | | |
| JP | 2005068367 A | 3/2005 | | |
| JP | 2005089674 A | 4/2005 | | |
| JP | 2008545630 A | 12/2008 | | |
| JP | 2010045281 A | 2/2010 | | |
| WO | WO-92/18552 A1 | 10/1992 | | |
| WO | WO-98/27136 A1 | 6/1998 | | |
| WO | WO-00/22026 A1 | 4/2000 | | |
| WO | WO-2004/041901 A1 | 5/2004 | | |
| WO | WO-2004/058911 A2 | 7/2004 | | |
| WO | WO-2004/070772 A2 | 8/2004 | | |
| WO | WO-2004/081017 A1 | 9/2004 | | |
| WO | WO-2004/113412 A2 | 12/2004 | | |
| WO | WO-2004/113468 A1 | 12/2004 | | |
| WO | WO-2005/011013 A1 | 2/2005 | | |
| WO | WO-2005/014689 A2 | 2/2005 | | |
| WO | WO-2005/040302 A1 | 5/2005 | | |
| WO | WO-2005/084081 A1 | 9/2005 | | |
| WO | WO-2005/084082 A1 | 9/2005 | | |
| WO | WO-2005/104264 A1 | 11/2005 | | |
| WO | WO-2006/100896 A1 * | 9/2006 | | C07C 211/61 |
| WO | WO-2006/100896 A1 | 9/2006 | | |
| WO | WO-2006/117052 A1 | 11/2006 | | |
| WO | WO-2006/122630 A1 | 11/2006 | | |
| WO | WO-2006/122630 A1 * | 11/2006 | | C09K 11/06 |
| WO | WO-2008/006449 A1 | 1/2008 | | |
| WO | WO-2008/056746 A1 | 5/2008 | | |
| WO | WO-2008/145239 A2 | 12/2008 | | |
| WO | WO-2009136595 A1 | 11/2009 | | |
| WO | WO-2009/148062 A1 | 12/2009 | | |

* cited by examiner

MATERIALS FOR ORGANIC ELECTROLUMINESCENCE DEVICES

RELATED APPLICATIONS

This application is a national stage application (under 35 U.S.C. §371) of PCT/EP2009/009220, filed Dec. 22, 2009, which claims the benefit of German Application No. 10 2009 005 289.5, filed Jan. 20, 2009.

The present invention describes indenofluorene derivatives containing heteroaromatic bridge atoms and amines in the para-position to the bridge atom as a novel class of materials having emitting and hole-transporting properties, in particular for use in the emission and/or charge-transport layer of electroluminescent devices. The invention furthermore relates to a process for the preparation of the compounds according to the invention and to electronic devices comprising same.

The general structure of organic electroluminescent devices is described, for example, in U.S. Pat. No. 4,539,507, U.S. Pat. No. 5,151,629, EP 0676461 and WO 98/27136. However, there is still a need for improvement in these devices:

1. The efficiency is still low, especially in the case of fluorescent OLEDs, and should be improved.
2. The operating lifetime is frequently still short, especially in the case of blue emission, so there is still a need for improvement here.
3. The operating voltage is fairly high, especially in the case of fluorescent OLEDs. A reduction in the operating voltage results in an improvement in the power efficiency. This is of major importance, in particular, for mobile applications.
4. In the case of hole-transport materials in accordance with the prior art, the voltage is dependent on the layer thickness of the hole-transport layer. In practice, a thicker layer thickness of the hole-transport layer would frequently be desirable. However, this can only be achieved with difficulty with materials in accordance with the prior art owing to the accompanying increase in voltage.
5. Some materials in accordance with the prior art exhibit the problem that they crystallise on the edge of the vapour-deposition source during vapour deposition and clog the vapour-deposition source here. These materials can therefore only be employed in mass production with significantly increased technical complexity.

Indenofluorenamines are used as charge-transport materials and -injection materials owing to very good hole mobility. This class of materials exhibits a comparatively low dependence of the voltage on the thickness of the transport layer. EP 1860097, WO 2006/100896, DE 102006025846, WO 2006/122630 and WO 2008/006449 disclose indenofluorenediamines for use in electronic devices. Good lifetimes on use as hole-transport material or as dark-blue emitters are cited therein. However, these compounds have the problem in mass production that, due to the crystallinity of the materials, they crystallise on the vapour-deposition source during vapour deposition and clog it. The use of these materials in production is therefore associated with increased technical complexity. Further improvements are therefore still desirable here.

There continues to be a demand, in particular, for improved emitting compounds, in particular blue-emitting compounds, which result in good efficiencies and at the same time in long lifetimes in organic electroluminescent devices and which can be processed without problems in industry. This applies equally to charge-transport and -injection compounds and to matrix materials for fluorescent or phosphorescent compounds. In particular, there is a need for improvement in the crystallinity of the materials.

The object of the present invention thus consists in the provision of such compounds.

Surprisingly, it has been found that electroluminescent devices which comprise indenofluorene derivatives, in particular derivatives containing heteroaromatic bridge atoms which are substituted by amines in the para-position to the bridge atoms, as blue-emitting dopants in a host material or as hole-transport compounds have significant improvements over the prior art. The improvement in the processability (reduction in crystallinity), the reduction in the operating voltage at the same time as increased hole mobility and the improvement in the colour coordinates on use as blue dopants are to the fore here. On use as hole-transport compounds, the replacement of carbon by heteroatoms in the bridges and the substitution by amines in the para-position to the bridge atoms enable a reduction in crystallinity and thus improved processability to be achieved. Furthermore, lower operating voltages, possibly owing to changes in the interfacial morphology, and a reduced dependence of the voltage on the charge-transport layer thickness owing to improved hole mobility arise. This applies, in particular, when the materials are used in layers having a relatively large layer thickness. On use as blue dopants, the compounds result in improved colour coordinates.

To this end, the invention provides a compound of the general formula I, II, III or IV:

formula I

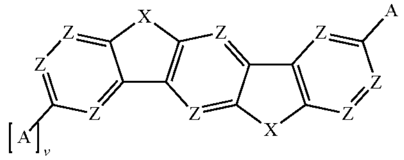

formula II

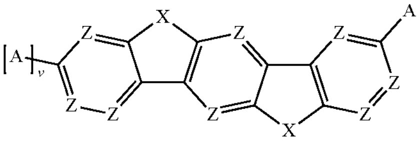

formula III

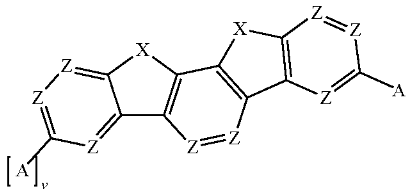

formula IV

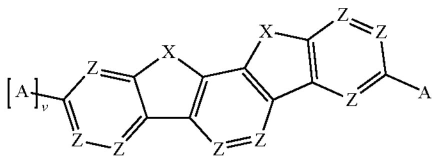

where

A corresponds to the general formula V formula V

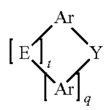

and where the link to the compound of the general formula I, II, III or IV takes place via Y;

Y is in each case, independently of one another, B, N, P, P═O, $PF_2$, P═S, As, As═O, As═S, Sb, Sb═O, Sb═S, Bi, Bi═O, Bi═S, C═O, O, S, Se, Te, S═O, $SO_2$, Se═O, $SeO_2$, Te═O or $TeO_2$, Z is in each case, independently of one another, CR or N;

X is in each case, independently of one another, a divalent bridge selected from $B(R^1)$, $C(R^1)_2$, $Si(R^1)_2$, C═O, C═$NR^1$, C═$C(R^1)_2$, O, S, S═O, $SO_2$, $N(R^1)$, $P(R^1)$ and P(═O)$R^1$;

R is in each case, independently of one another, H, D, F, Cl, Br, I, $N(R^2)_2$, $N(Ar)_2$, C(═O)Ar, P(═O)$Ar_2$, S(═O)Ar, S(═O)$_2$Ar, $CR^2$═$CR^2$Ar, CN, $NO_2$, $Si(R^2)_3$, $B(OR^2)_2$, $OSO_2R^2$, a straight-chain alkyl, alkenyl, alkynyl, alkoxy or thioalkoxy group having 1 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by $R^2C$═$CR^2$, C≡C, $Si(R^2)_2$, $Ge(R^2)_2$, $Sn(R^2)_2$, C═O, C═S, C═Se, C═$NR^2$, P(═O)($R^2$), SO, $SO_2$, $NR^2$, O, S or $CONR^2$ and where one or more H atoms may be replaced by F, Cl, Br, I, CN or $NO_2$, or an aromatic or heteroaromatic ring system having 5 to 40 aromatic ring atoms, which may in each case be substituted by one or more radicals $R^2$, or an aryloxy or heteroaryloxy group having 5 to 40 aromatic ring atoms, which may be substituted by one or more radicals $R^2$, or a combination of these systems, where two or more substituents R may also form a mono- or polycyclic aliphatic ring system with one another;

$R^1$ is in each case, independently of one another, H, D, F, Cl, Br, I, CN, $NO_2$, $N(R^2)_2$, $B(OR^2)_2$, $Si(R^2)_3$, a straight-chain alkyl, alkenyl, alkynyl, alkoxy or thioalkoxy group having 1 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by —$R^2C$═$CR^2$—, —C≡C—, $Si(R^2)_2$, $Ge(R^2)_2$, $Sn(R^2)_2$, C═O, C═S, C═Se, C═$NR^2$, —O—, —S—, —COO— or —$CONR^2$— and where one or more H atoms may be replaced by F, Cl, Br, I, CN or $NO_2$, or arylamines or substituted carbazoles, each of which may be substituted by one or more radicals $R^2$, or an aromatic or heteroaromatic ring system having 5 to 40 aromatic ring atoms, which may be substituted by one or more non-aromatic radicals $R^2$, or an aryloxy or heteroaryloxy group having 5 to 40 aromatic ring atoms, which may be substituted by one or more non-aromatic radicals $R^2$, or a combination of these systems, where two or more substituents $R^1$ may also form a mono- or polycyclic ring system with one another;

$R^2$ is in each case, independently of one another, H, D or an aliphatic or aromatic hydrocarbon radical having 1 to 20 C atoms;

Ar is in each case, independently of one another, an aromatic or heteroaromatic ring system having 5 to 40 aromatic ring atoms, which may be substituted by one or more radicals $R^1$;

E is in each case, independently of one another, a single bond, $N(R^1)$, O, S, $C(R^1)_2$, $Si(R^1)_2$ or $B(R^1)$;

q=1 if the corresponding central atom of the group Y is an element from main group 3 or 5 and ═O if the corresponding central atom of the group Y is an element from main group 4 or 6;

t is in each case, independently of one another, 0 or 1, where t=0 if q=0, and where t=0 means that a group $R^1$ is bonded instead of E;

v is in each case, independently of one another, 0 or 1, where v=0 means that a radical R is bonded instead of the Group A.

In an embodiment of the invention, it is preferred for the radical Y in the compounds of the general formula I, II, III or IV to be in each case, independently of one another, N or C═O.

It is furthermore preferred for X to be selected, identically or differently on each occurrence, from $N(R^1)$, S or $C(R^1)_2$, where $R^1$ has the meaning indicated above.

In still a further embodiment of the invention, it is preferred for the group Z to be in each case, independently of one another, CR. The radical R here preferably has the meaning indicated above.

In still a further embodiment of the invention, it is preferred for Ar in the compounds of the general formula I, II, III or IV to be phenyl, naphthyl, a substituted aromatic or heteroaromatic ring system having 5-15 carbon atoms or an aromatic or heteroaromatic ring system which is substituted by arylamine or carbazole.

In still a further embodiment of the invention, E is not present, i.e. t=0, or E is a single bond or $C(R^1)_2$, where $R^1$ has the meaning indicated above.

It is furthermore preferred for the index v=1 in the compounds of the general formula I, II, III or IV.

In still a further embodiment of the invention, the compound is selected from the formulae Ia, IIa, IIIa and IVa:

formula Ia

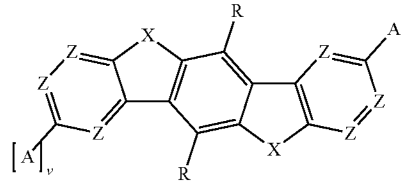

formula IIa

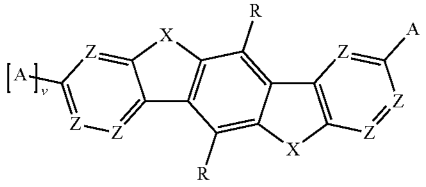

formula IIIa

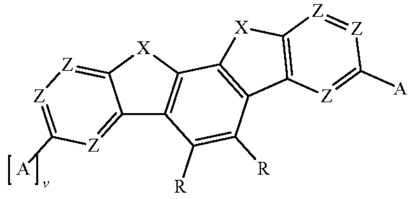

-continued formula IVa

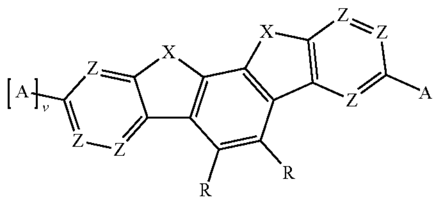

where the symbols and indices have the meanings indicated above.

In still a further embodiment of the invention, the compound is selected from the formulae Ib, IIb, IIIb and IVb:

formula Ib

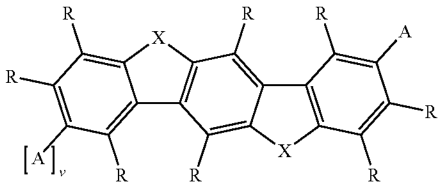

formula IIb

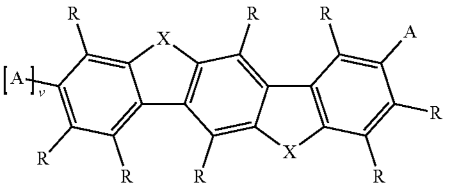

formula IIIb

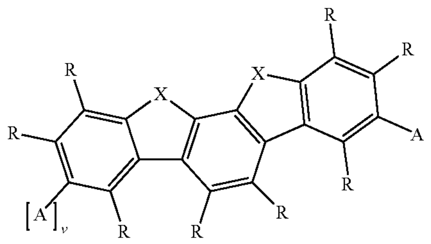

formula IVb

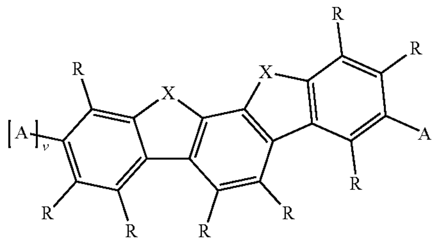

where the symbols and indices have the meanings indicated above.

In a preferred embodiment of the invention, the symbol X in the compounds of the formula Ia, IIa, IIIa or IVa, or Ib, IIb, IIIb or IVb stands, identically or differently on each occurrence, for $NR^1$ or $C(R^1)_2$, and the symbol Y which occurs in the group A stands for C═O or N.

For the purposes of the invention, it is furthermore preferred for the compound of the general formula I, II, III or IV to conform to the formula VI, VII, VIII or IX:

formula VI

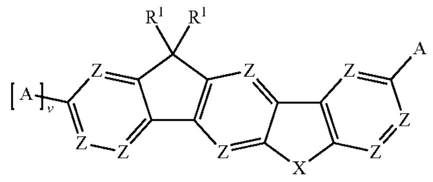

formula VII

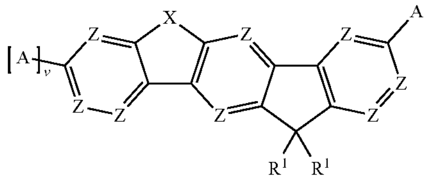

formula VIII

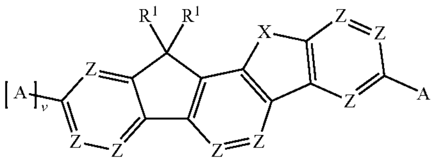

formula IX

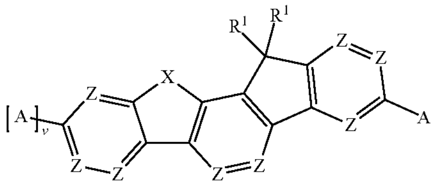

where the symbols and indices have the meanings indicated above.

In still a further embodiment of the invention, the compound is selected from the formulae VIa, VIIa, VIIIa and IXa:

formula VIa

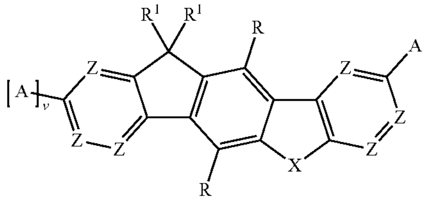

formula VIIa

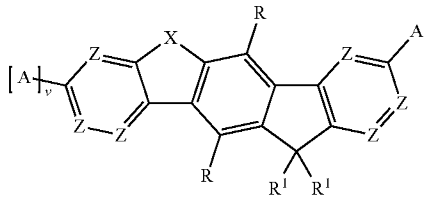

-continued formula VIIIa

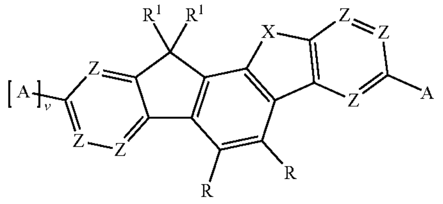

formula IXa

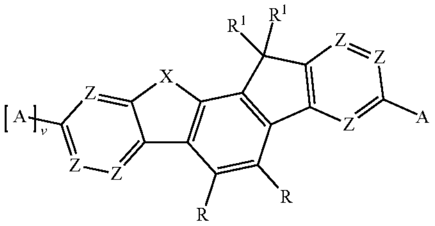

where the symbols and indices have the meanings indicated above.

In still a further embodiment of the invention, the compound is selected from the formulae VIb, VIIb, VIIIb and IXb:

formula VIb

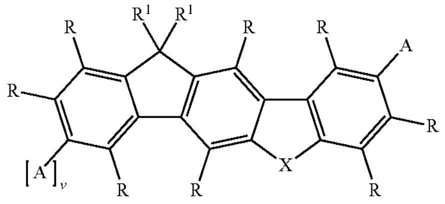

-continued formula VIIb

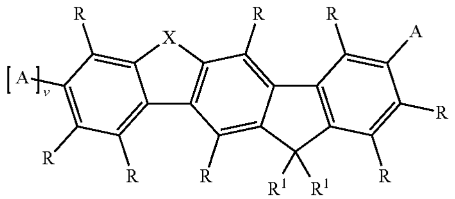

formula VIIIb

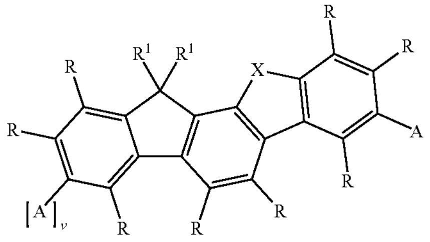

formula IXb

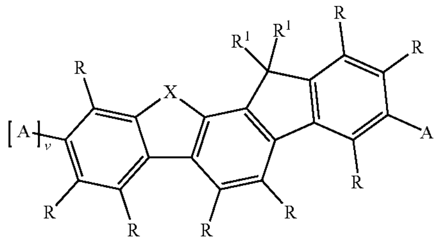

where the symbols and indices have the meanings indicated above.

It is furthermore preferred for the compounds according to the invention to satisfy the following structural formulae 1 to 92.

1

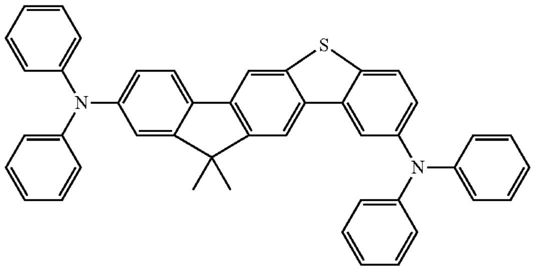

2

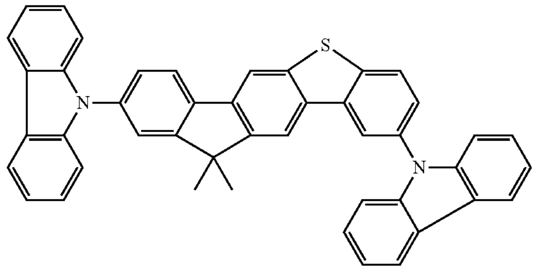

3

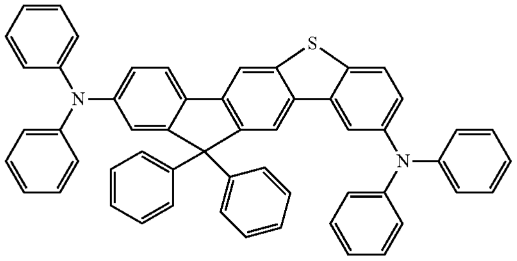

4

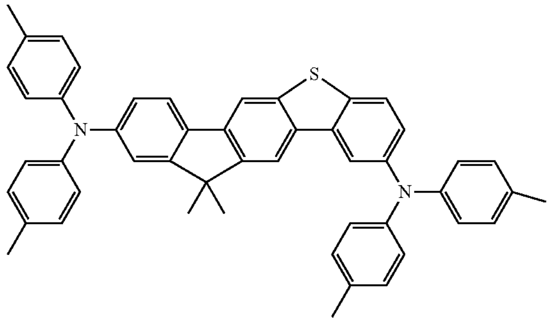

-continued
5
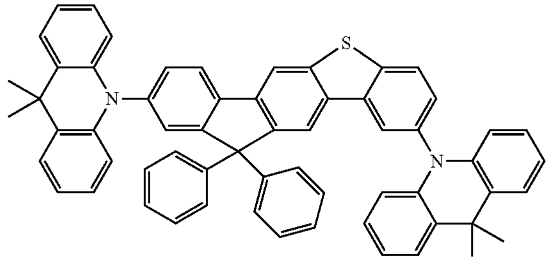
6
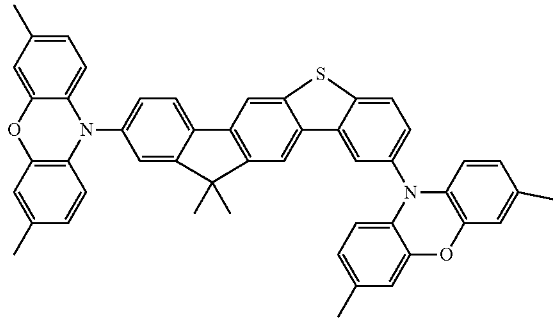
7
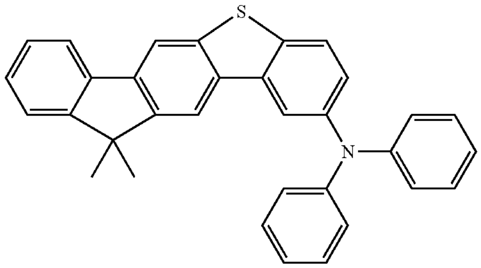
8
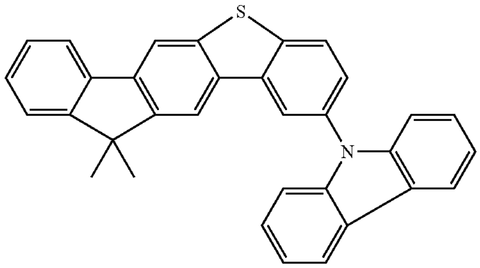
9
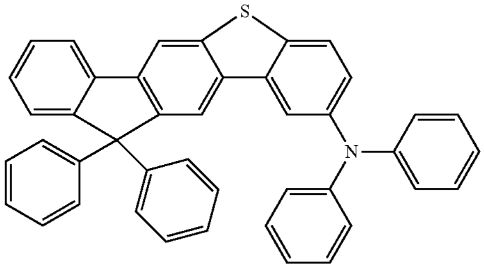
10
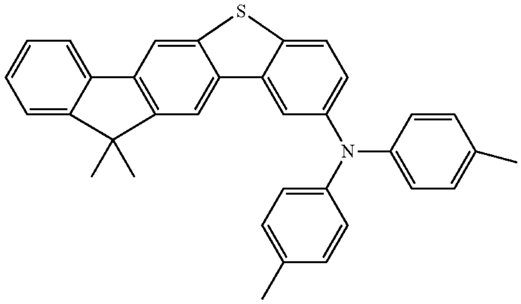
11
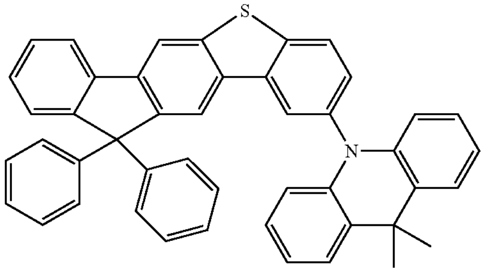
12
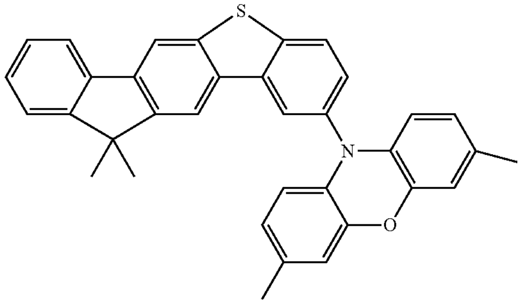
13
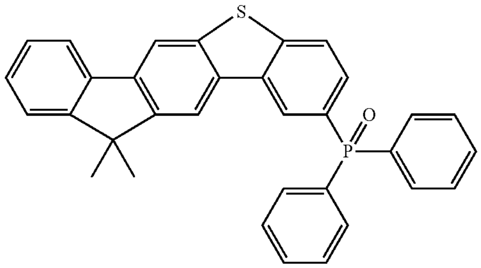
14
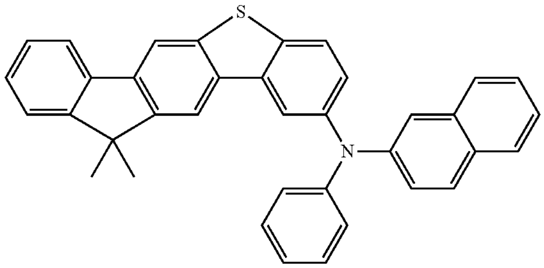

-continued
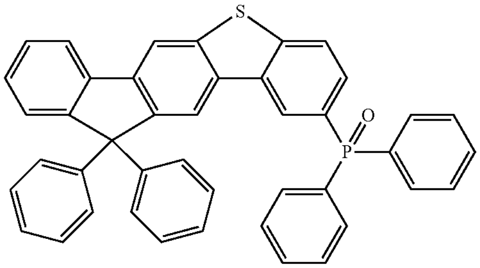
15
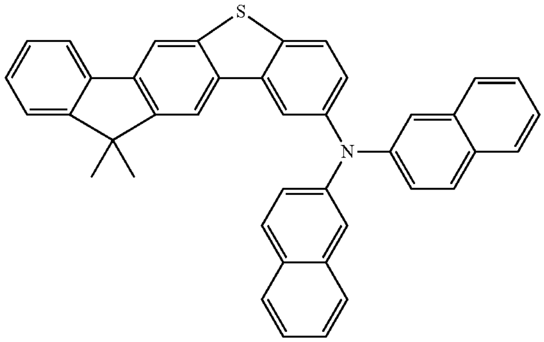
16
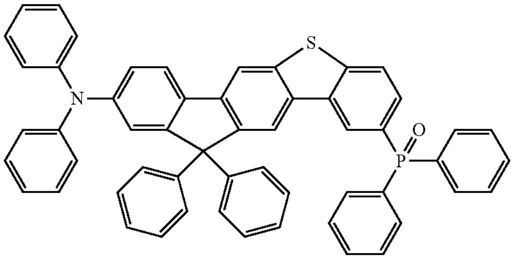
17
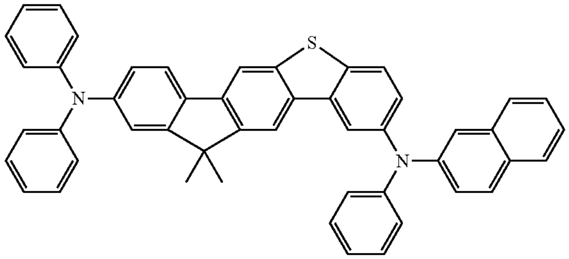
18
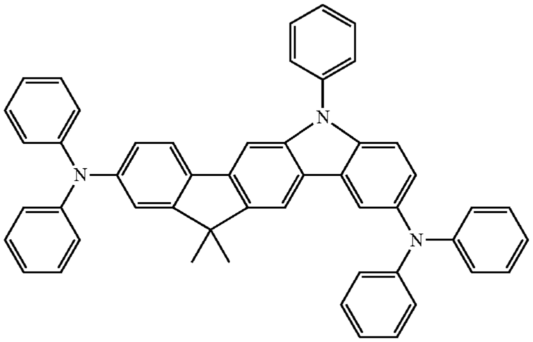
19
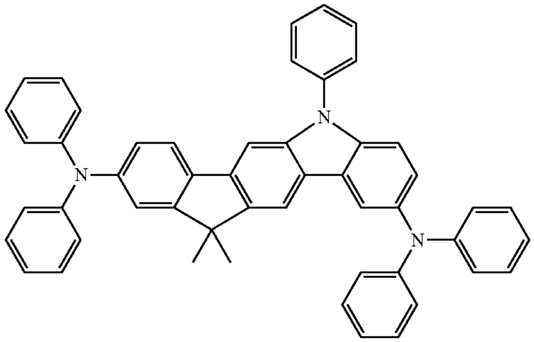
20
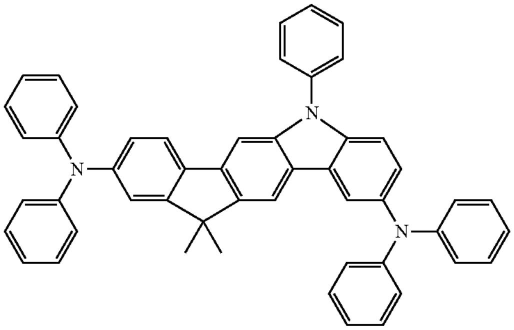
21
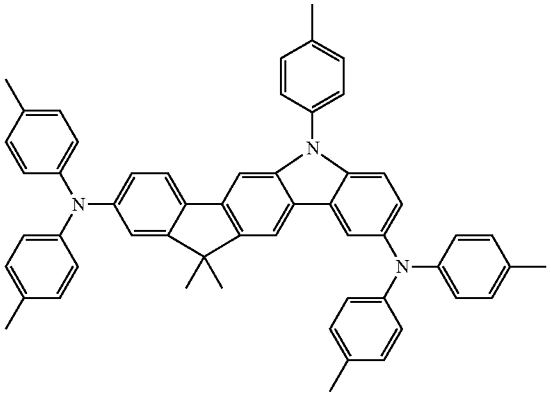
22

-continued
23
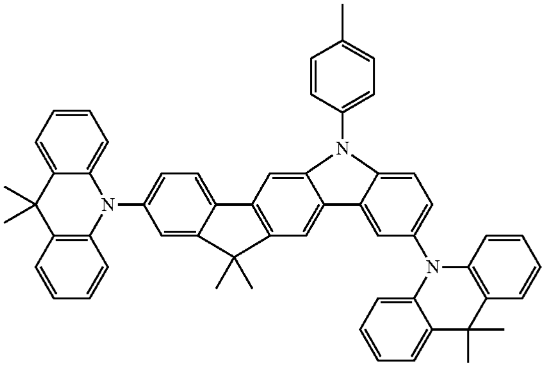
24
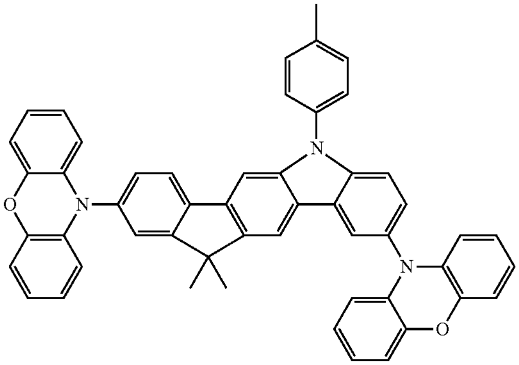
25
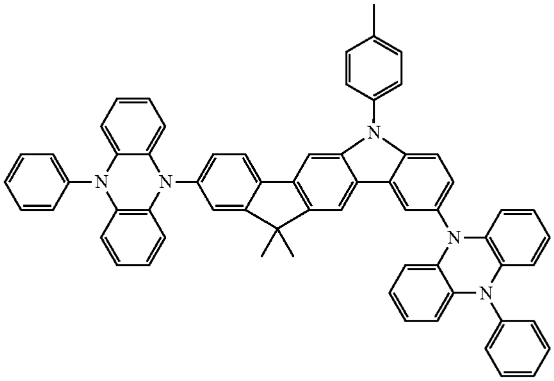
26
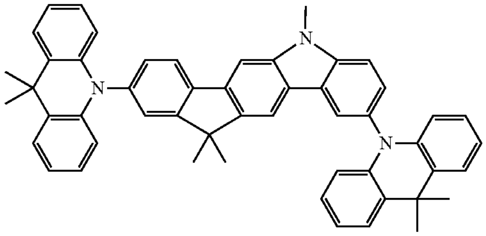
27
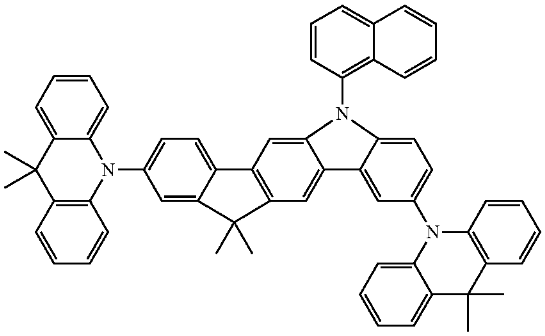
28
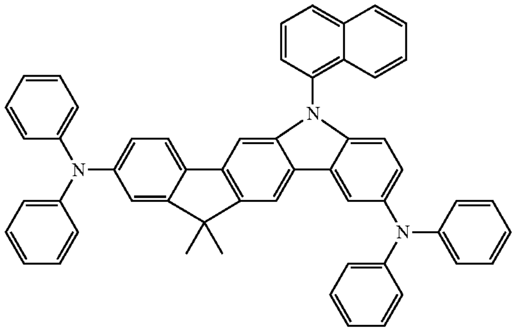
29
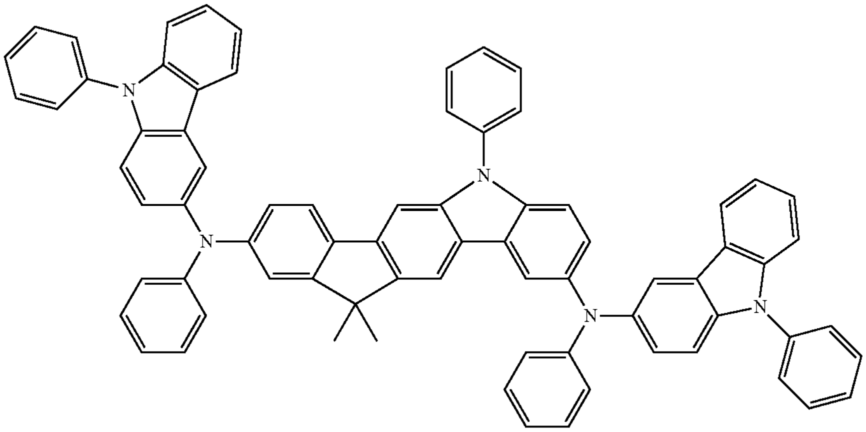

-continued
30
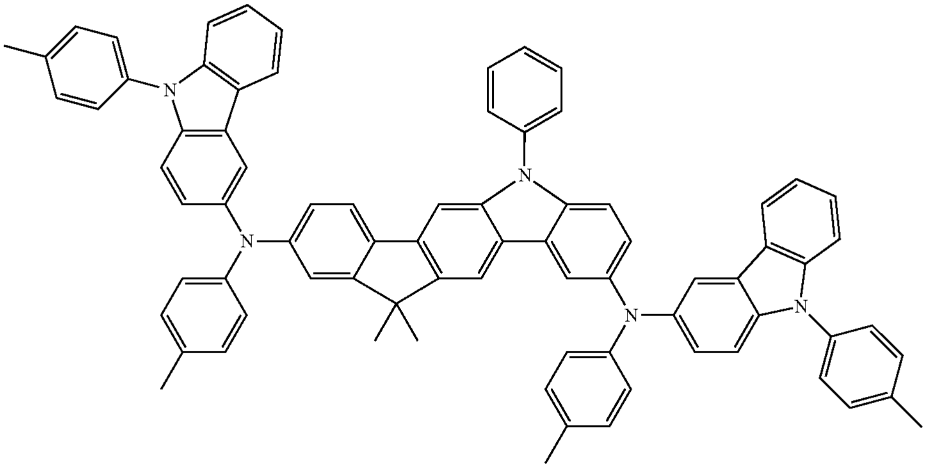
31
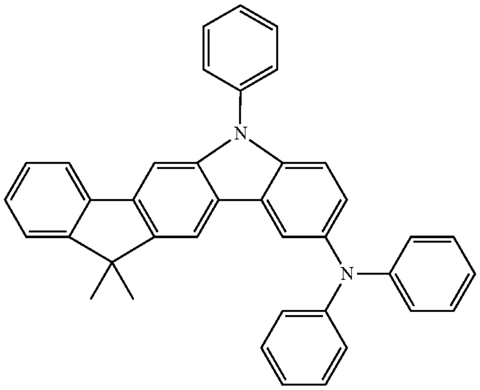
32
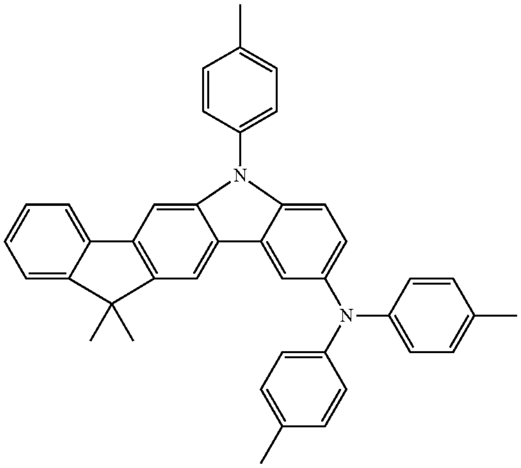
33
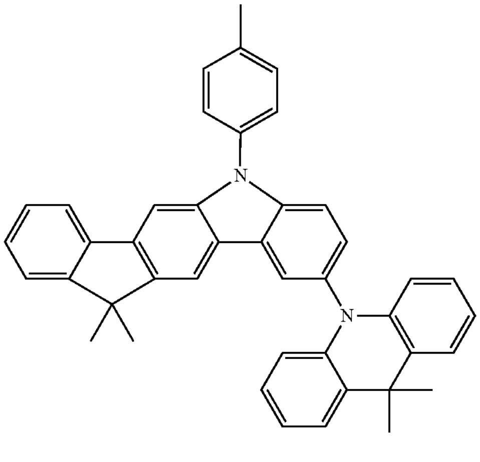
34
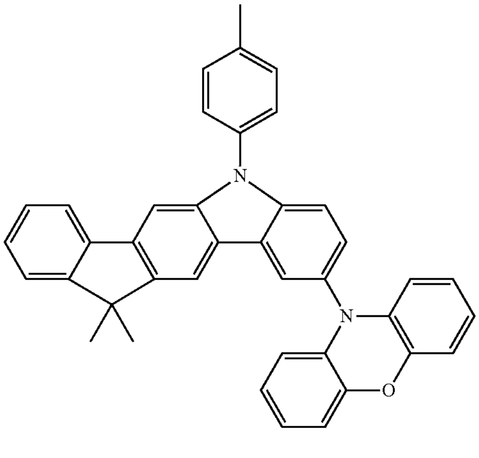

-continued
35
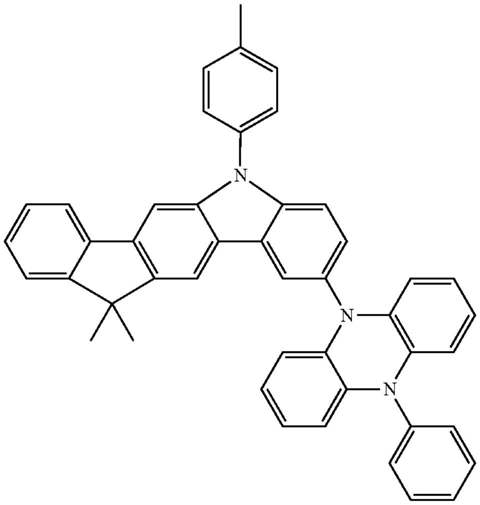
36
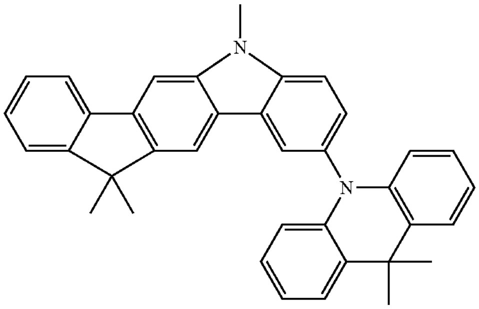
37
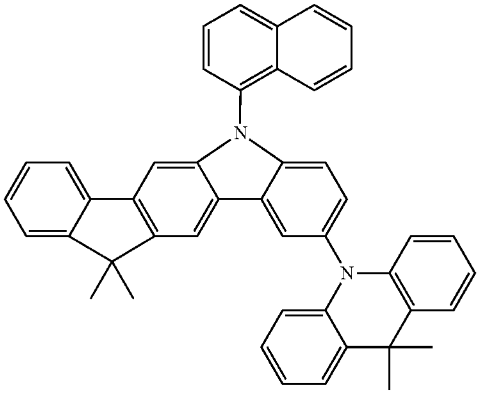
38
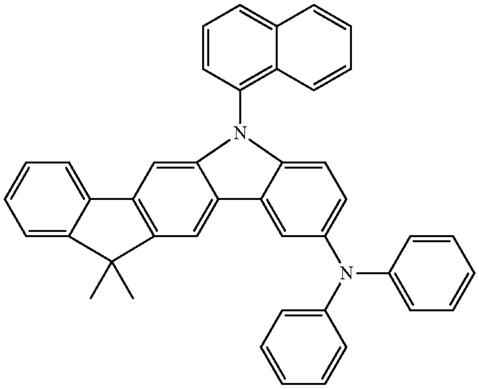
39
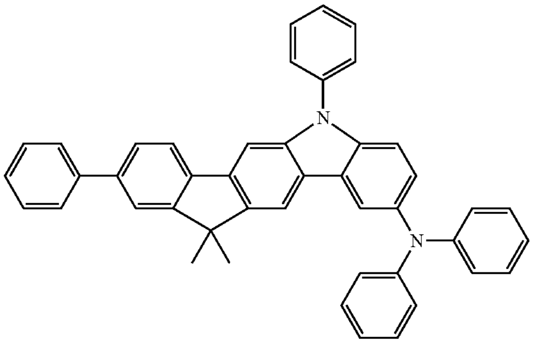
40
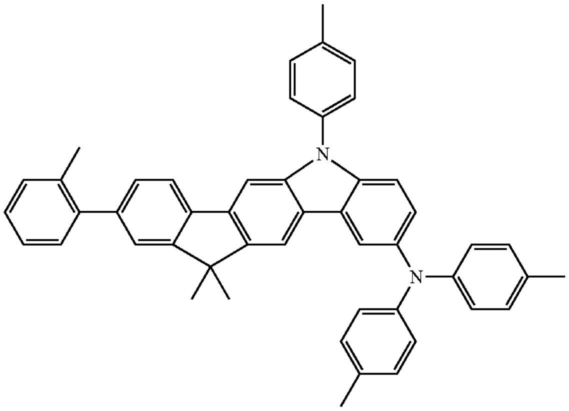

-continued
41
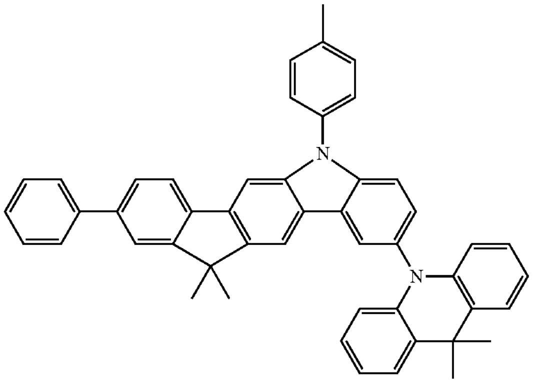
42
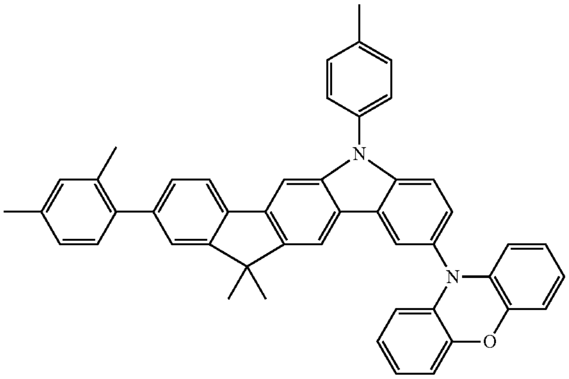
43
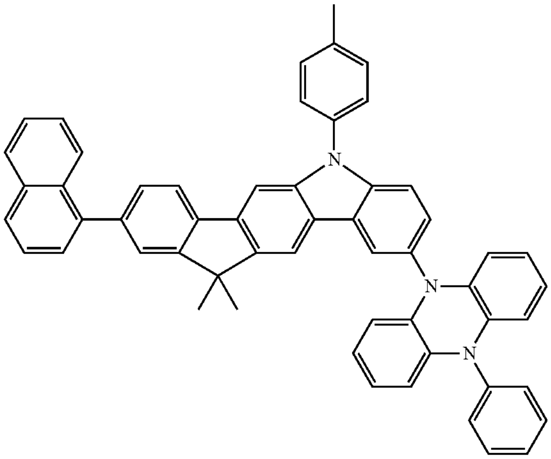
44
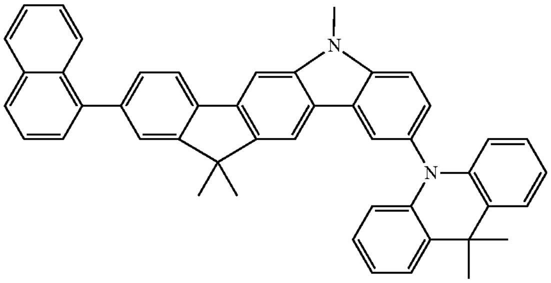
45
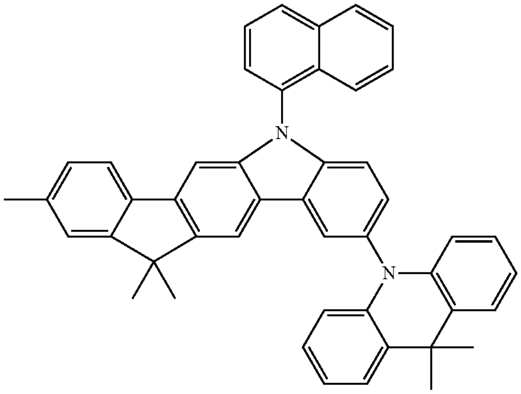
46
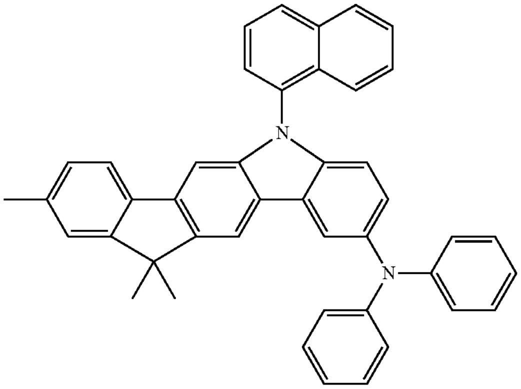
47
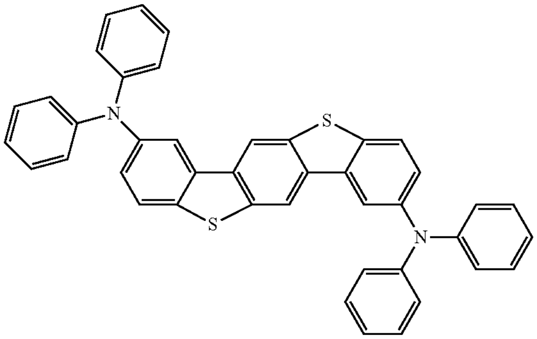
48
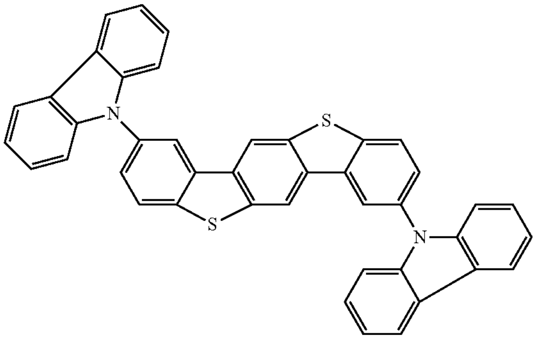

-continued
49
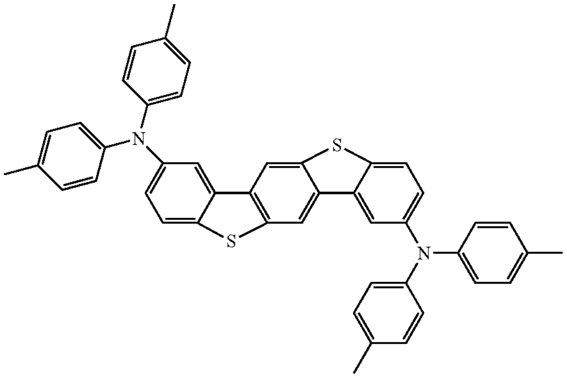
50
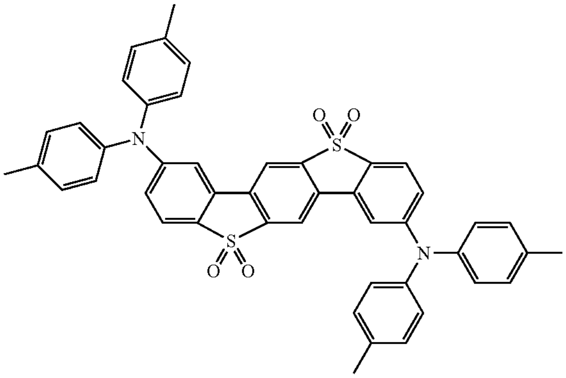
51
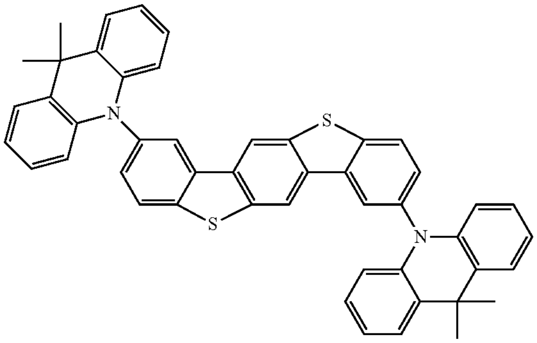
52
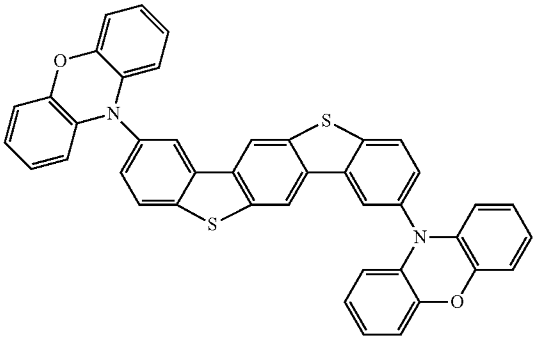
53
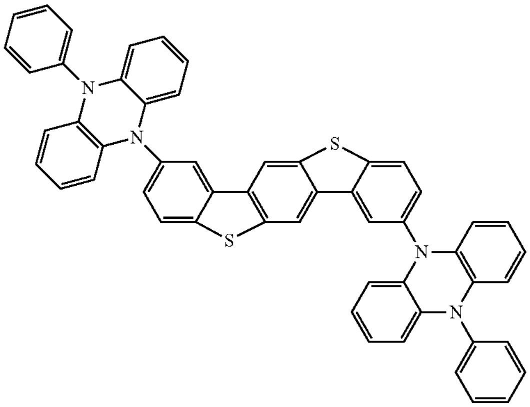
54
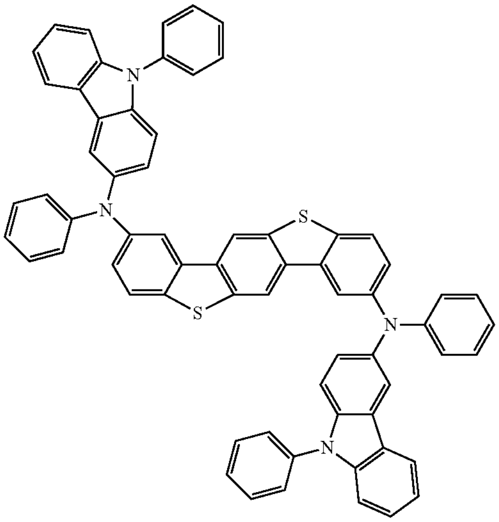

-continued
55
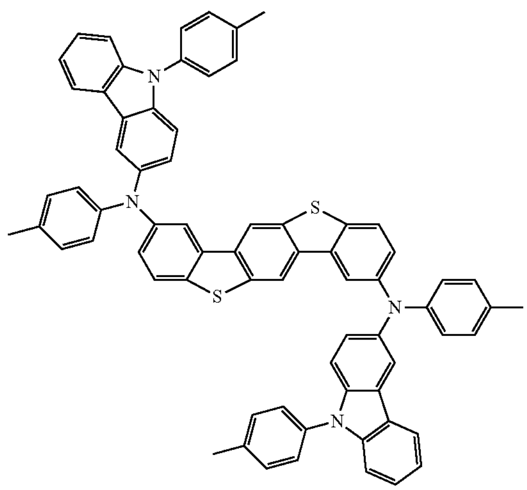
56
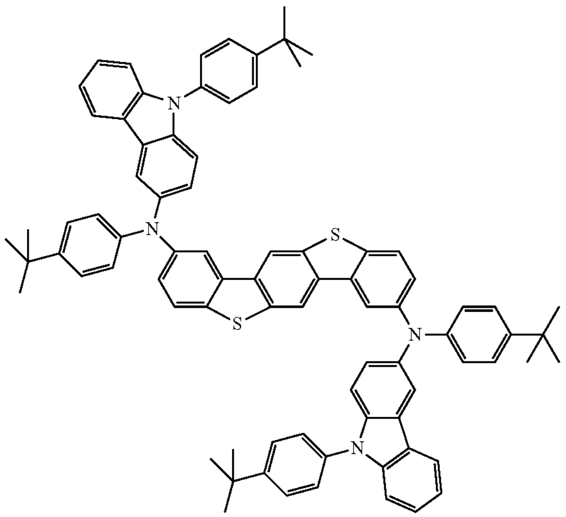
57
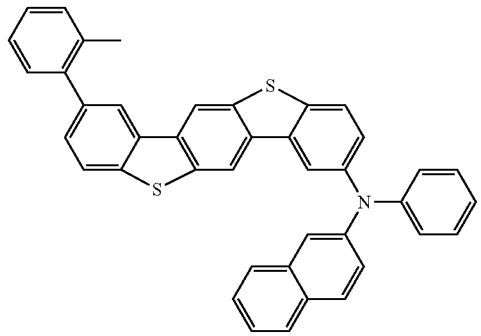
58
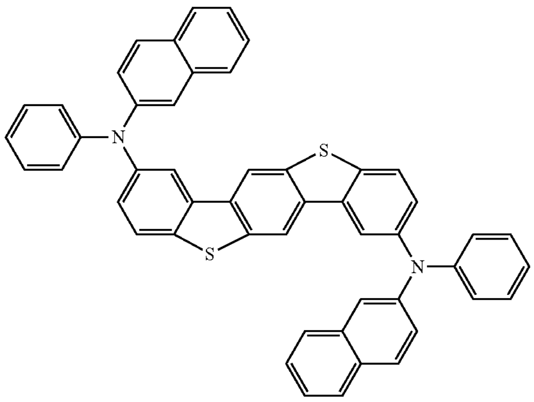
59
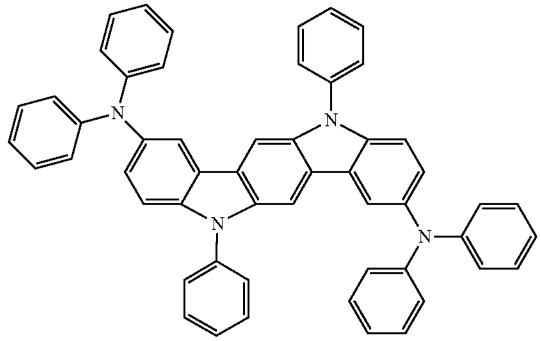
60
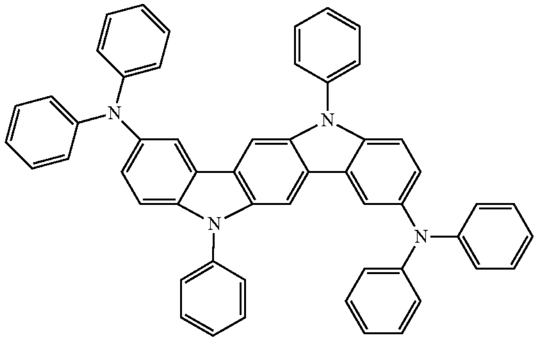
61
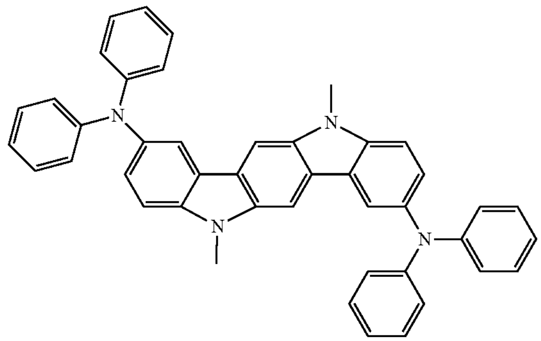
62
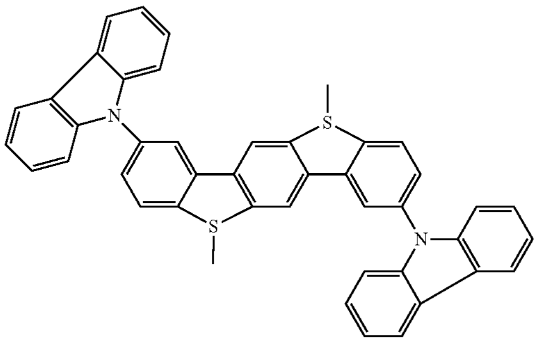

-continued
63
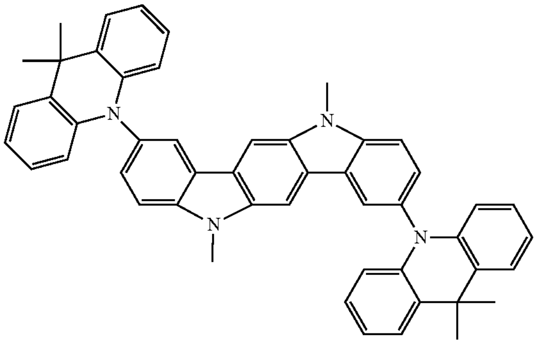
64
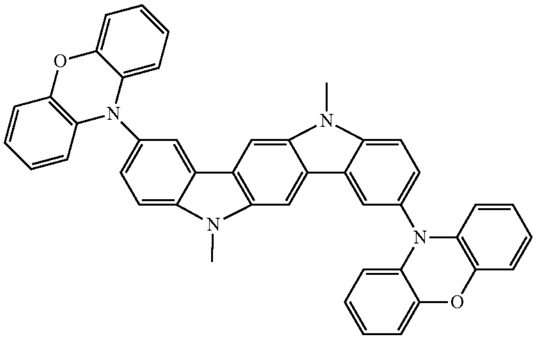
65
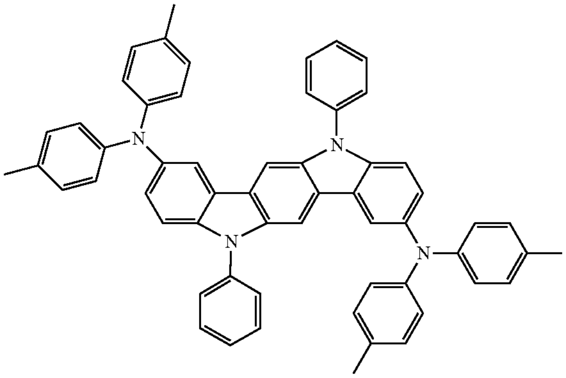
66
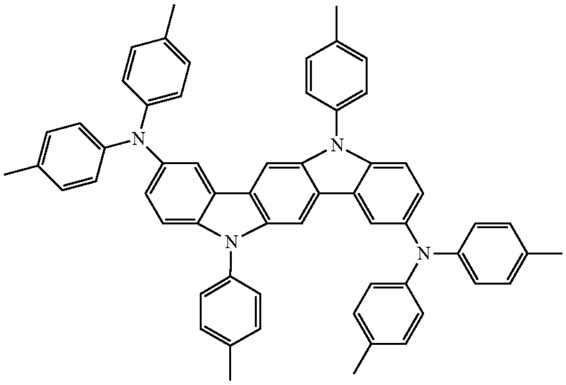
67
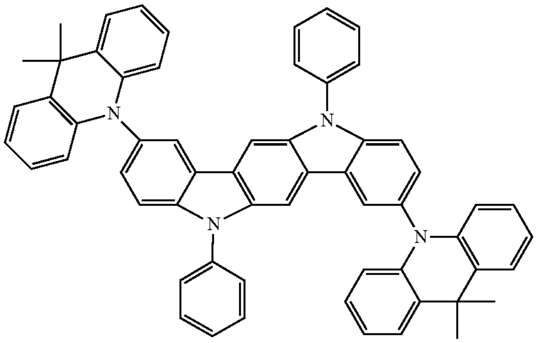
68
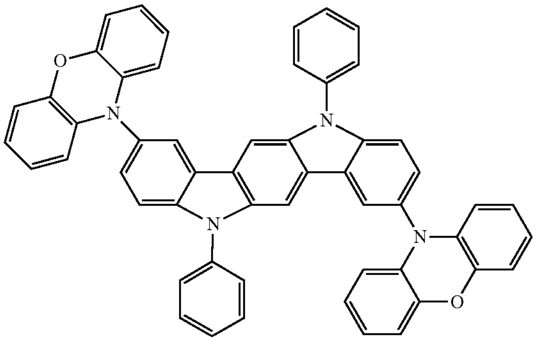
69
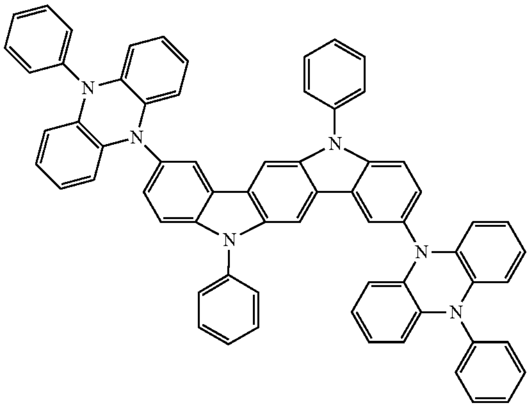
70
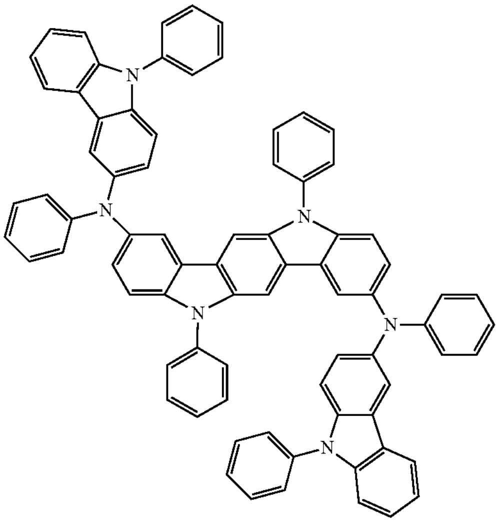

-continued
71
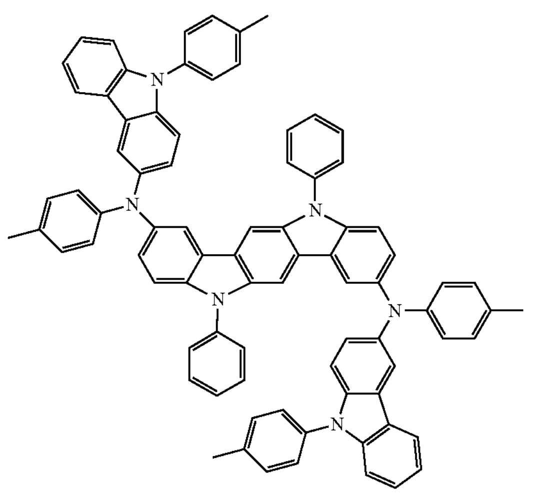
72
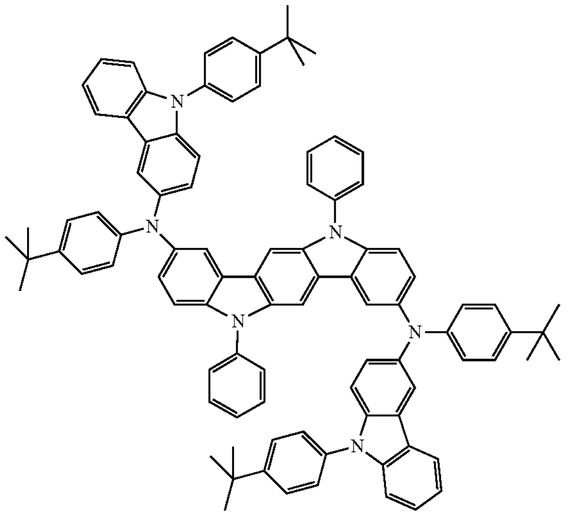
73
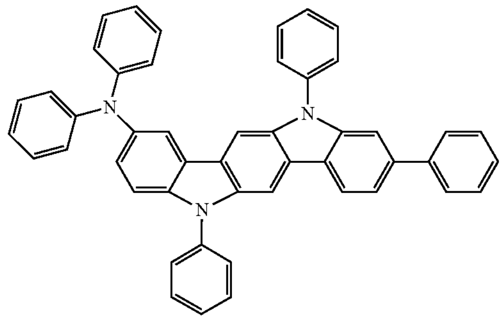
74
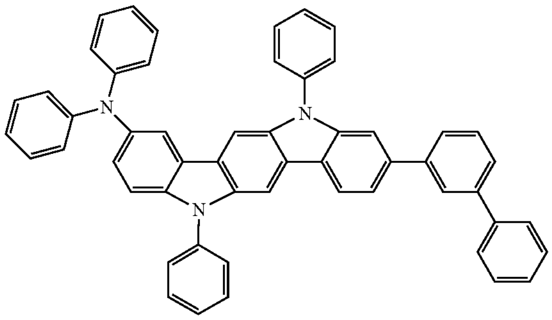
75
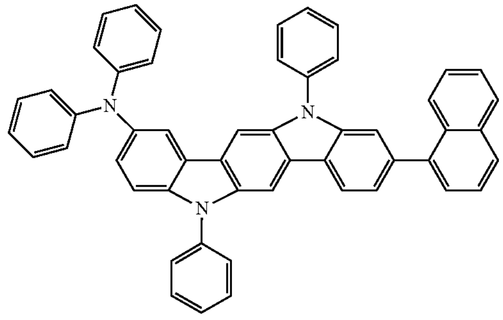
76
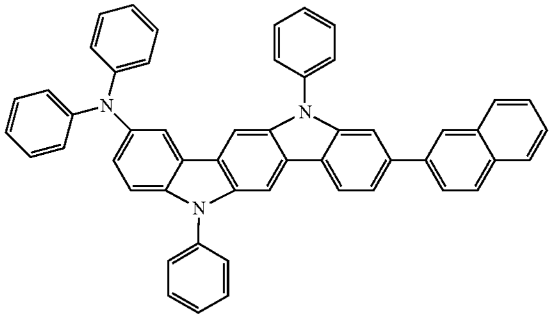
77
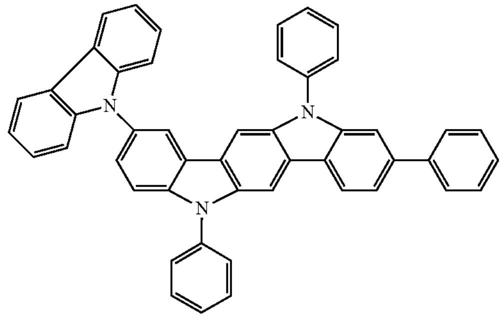
78
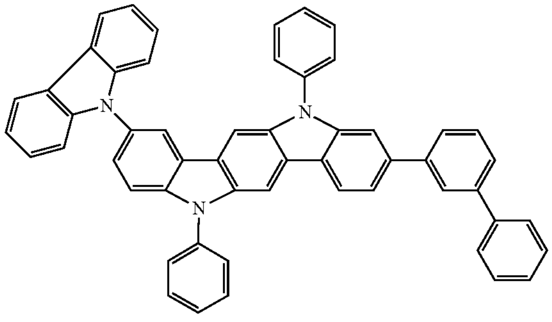

-continued
79
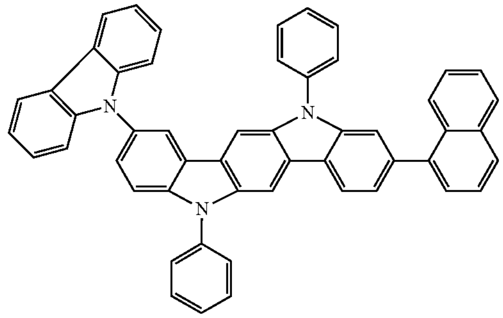
80
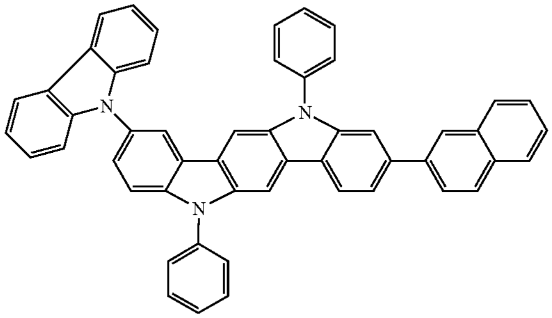
81
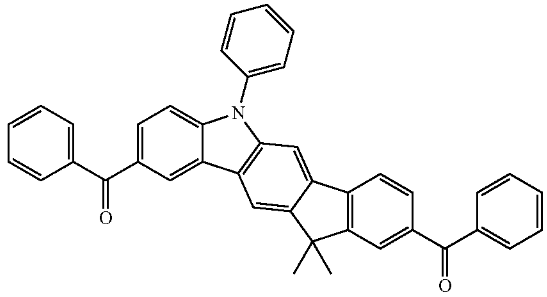
82
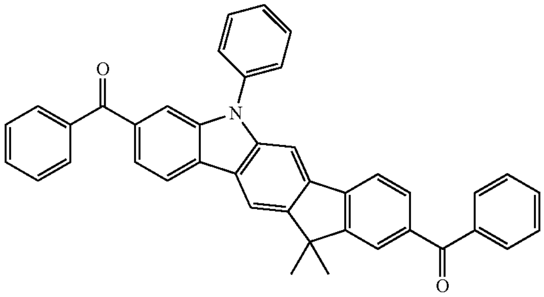
83
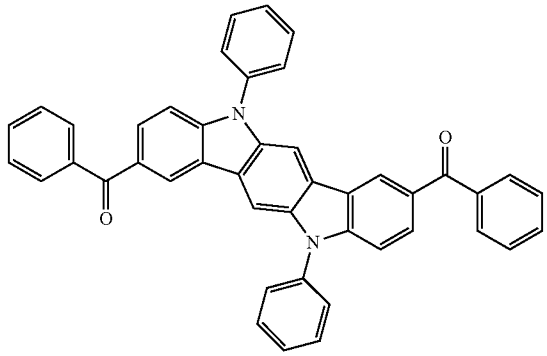
84
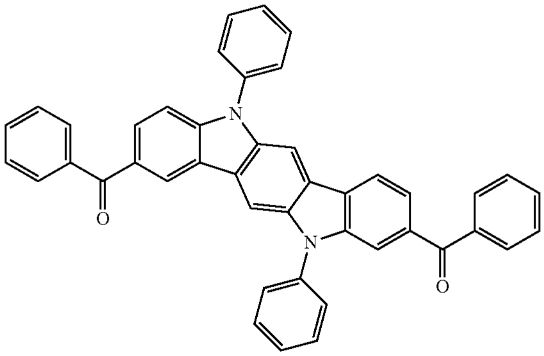
85
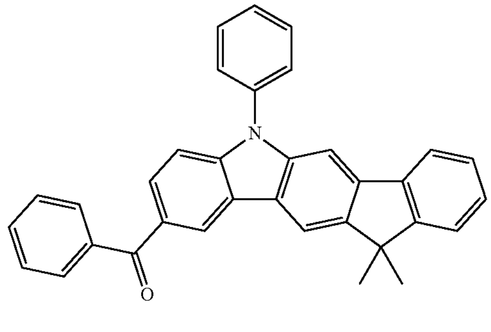
86
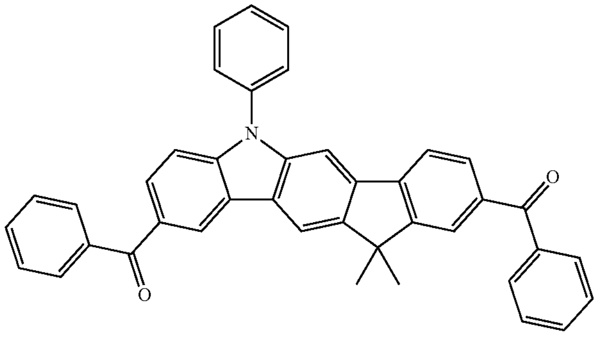

-continued
87
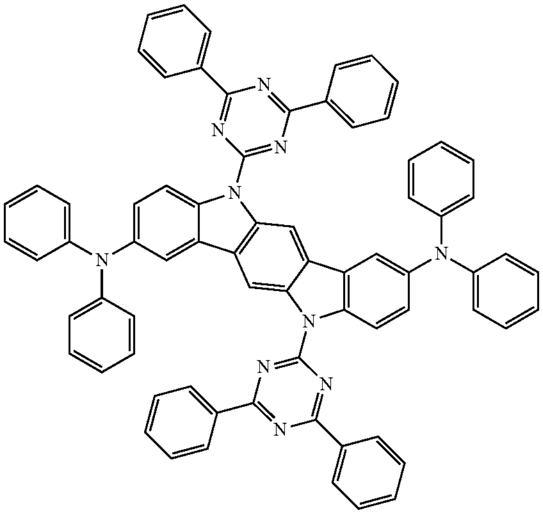
88
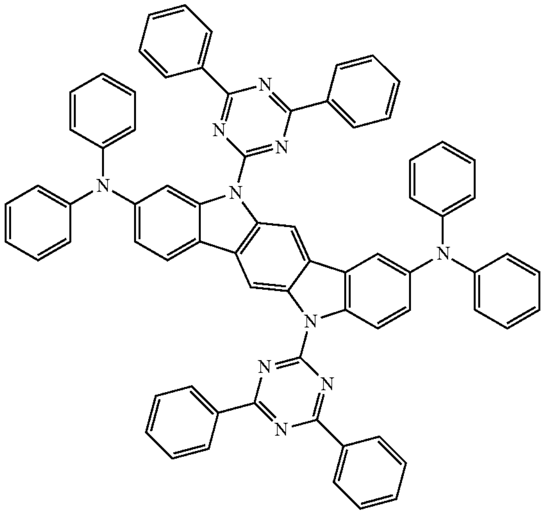
89
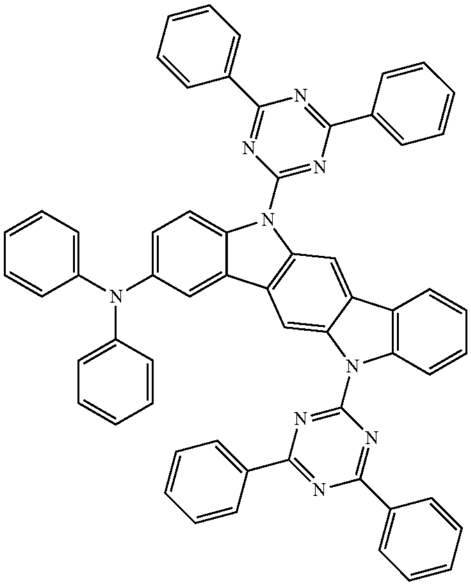
90
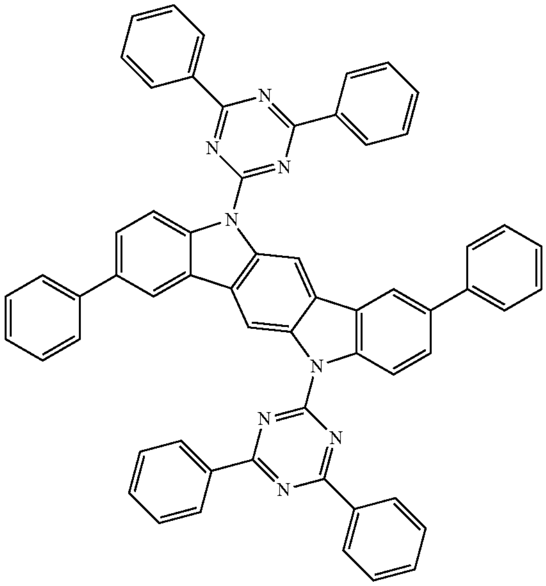
91
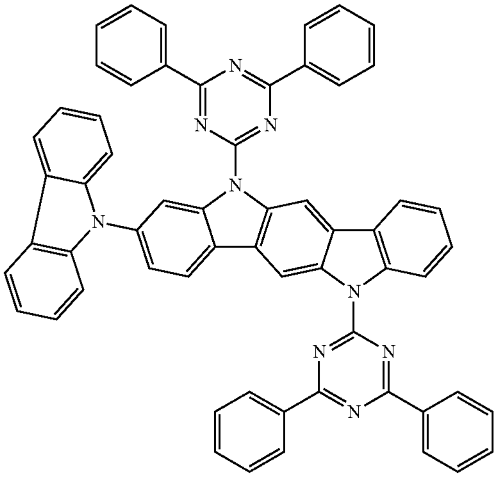
92
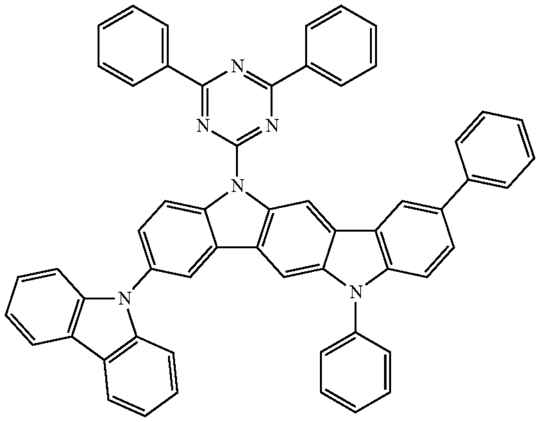
For the purposes of the present invention, an alkyl group having 1 to 40 C atoms, in which, in addition, individual H atoms or $CH_2$ groups may be substituted by the groups mentioned above in the definition of $R^1$, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoro-methyl, pentafluoroethyl or 2,2,2-trifluoroethyl. For the purposes of this invention, an alkenyl group is taken to mean, for example, ethenyl, propenyl, butenyl, pentenyl, cyclopentenyl, hexenyl, cyclohexenyl, heptenyl, cycloheptenyl, octenyl or cyclooctenyl. For the purposes of this invention, an alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

For the purposes of this invention, an aryl group preferably contains 5 to 40 C atoms; for the purposes of this invention, a heteroaryl group contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, benzanthracene, phenanthrene, pyrene, perylene, quinoline, isoquinoline, benzothiophene, benzofuran and indole, etc.

For the purposes of this invention, an aromatic ring system contains 5 to 40 C atoms in the ring system. For the purposes of this invention, a heteroaromatic ring system contains 2 to 40 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, etc. are also intended to be taken to be aromatic ring systems for the purposes of this invention, as are systems in which two or more aryl groups are interrupted, for example, by a linear or cyclic alkyl group or by a silyl group.

An aromatic or heteroaromatic ring system having 5-60 aromatic ring atoms, which may also in each case be substituted by the above-mentioned radicals R and which may be linked to the aromatic or heteroaromatic ring system via any desired positions, is taken to mean, in particular, groups derived from benzene, naphthalene, anthracene, phenanthrene, benzanthracene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetra-hydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The compounds according to the invention can be prepared by synthetic steps known to the person skilled in the art, such as, for example, bromination, Suzuki coupling, Hartwig-Buchwald coupling, etc.

Thus, the indenofluorene precursors can be prepared, for example, as depicted in Synthesis Scheme 1: Suzuki coupling of a benzeneboronic acid and a substituted 1,4-dibromobenzene compound, followed by ring closure, for example under the action of a strong acid, and reduction gives the unsubstituted trans-indenofluorene, which can be alkylated using alkylating agents. This can either be halogenated, for example brominated, or converted into the corresponding amino compound by nitration and reduction. Bis(diarylamino)indenofluorenes can be synthesised by Hartwig-Buchwald coupling of the dibromo compound, as shown in Synthesis Scheme 2.

Phosphines or phosphine oxides containing indenofluorene can be synthesised from dibromoindenofluorene by lithiation and reaction with diaryl-chlorophosphines, as shown in Synthesis Scheme 3. Oxidation then gives the corresponding phosphine oxide. It is likewise possible to employ other electrophiles here, such as, for example, $AsCl_3$, aryl$PCl_2$, $SOCl_2$, $Ar_2S_2$, etc. Further compounds according to the invention can easily be synthesised by these and similar synthesis schemes in processes known to the person skilled in the art of organic synthesis. Furthermore, the compounds obtained can be brominated by standard methods and thus employed as monomers for polymers, oligomers or dendrimers.

The invention furthermore relates to a process for the preparation of a compound of the general formula I, II, III or IV, characterised by the steps of:

a) carrying out of a metal-catalysed cross-coupling reaction of an $X^1$-substituted aromatic or heteroaromatic dihalogen compound with further aromatic or heteroaromatic compounds, which are optionally substituted by A,
b) formation of a divalent bridge —X— between the coupled aromatic or heteroaromatic compounds, where X has the meaning indicated above. $X^1$ represents a precursor of the divalent bridge X, i.e. can be converted into X by standard methods of organic chemistry. $X^1$ is furthermore selected so that the ring-closure reaction is facilitated.

The aromatic or heteroaromatic dihalogen compound is preferably a 1,4-dibromobenzene compound, which is preferably substituted by $X^1$ in the ortho-position to the halogens, for the generation of trans derivatives, or a corresponding 1,2-dibromobenzene compound for the generation of cis derivatives.

The optionally A-substituted aromatic or heteroaromatic compounds preferably carry a boronic acid or boronic acid ester functionality.

After successful ring closure, X forms a divalent bridge between the aromatic or heteroaromatic components (see Synthesis Scheme 1). A carboxylate group or an acetyl group, for example, is suitable as group $X^1$ here, which can then be converted into a bridge X=carbon in the ring-closure reaction. A nitro group is furthermore suitable as group X', which can then be converted into a bridge X=nitrogen in the ring-closure reaction. A thioether group, in particular an alkylthioether group, is furthermore suitable as group $X^1$, which can then be converted into a bridge X=sulfur in the ring-closure reaction. The divalent bridge X may subsequently be substituted by further radicals, for example by alkyl or aryl groups or generally by $R^1$ as defined above. The indenofluorene compound prepared in this way can then be functionalised, for example halogenated, preferably brominated, in a further step. A functional group is thus available for the introduction of the radicals shown in Synthesis Schemes 2 and 3.

Synthesis Scheme 1: Precursors of indenofluorene derivatives

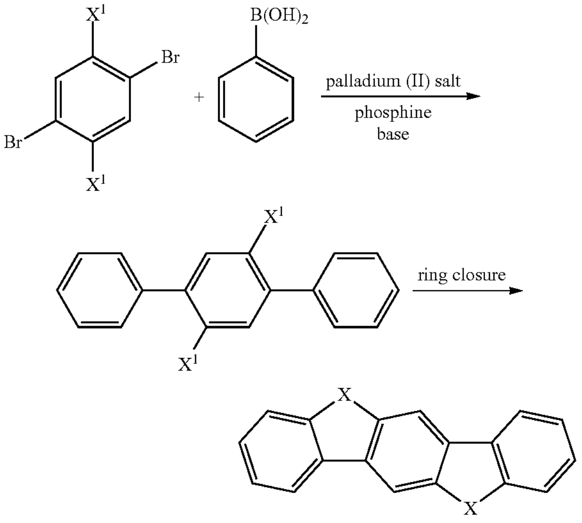

Synthesis Scheme 2: Amination

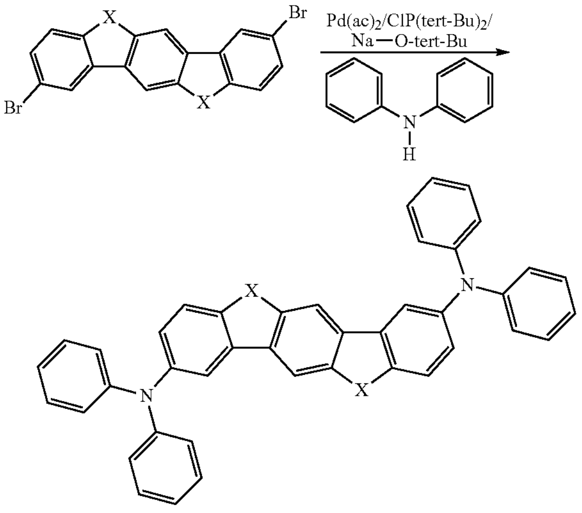

Synthesis Scheme 3: Synthesis of the phosphine oxide derivative

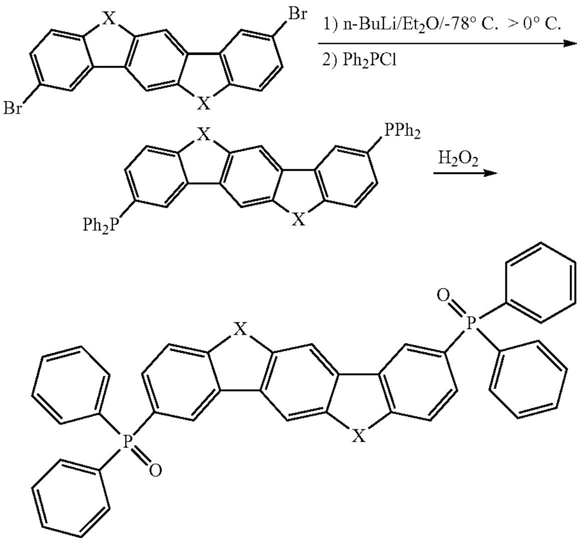

Electrophiles which can be reacted analogously: $AsCl_3$, $SbCl_3$, $BiCl_3$, $arylPCl_2$, $aryl_2PCl$, $SCl_2$, $SOCl_2$, $SO_2Cl_2$, $Ar_2S_2$, $Ar_2Se_2$, $Ar_2Te_2$, etc.

The compounds of the formula I, II, III or IV can be employed in organic electroluminescent devices. The precise use of the compounds depends on the substituents.

In a preferred embodiment of the invention, the compound of one of the formulae I, II, III or IV is employed in an emitting layer, preferably in a mixture with at least one further compound. It is preferred for the compound of one of the formulae I, II, III or IV to be the emitting compound (the dopant) in the mixture. Preferred host materials are organic compounds whose emission is of shorter wavelength than that of the compound of one of the formulae I, II, III or IV or which do not emit at all.

The invention therefore furthermore relates to mixtures of one or more compounds of one of the formulae I, II, III or IV with one or more host materials.

The proportion of the compound of one of the formulae I, II, III or IV in the mixture of the emitting layer is between 0.1 and 99.0% by vol., preferably between 0.5 and 50.0% by vol., particularly preferably between 1.0 and 20.0% by vol., in particular between 1.0 and 10.0% by vol. Correspondingly, the proportion of the host material in the layer is between 1.0 and 99.9% by vol., preferably between 50.0 and 99.5% by vol., particularly preferably between 80.0 and 99.0% by vol., in particular between 90.0 and 99.0% by vol.

Suitable host materials are various classes of substance. Preferred host materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 or WO 05/084082), the atropisomers (for example in accordance with EP 1655359), the boronic acid derivatives (for example in accordance with WO 06/117052) or the benzanthracenes (for example in accordance with WO 08/145,239). Particularly preferred host materials are selected from the classes of the oligoarylenes, comprising naphthalene, anthracene, benzanthracene and/or pyrene, or atropisomers of these compounds, the oligoarylenevinylenes, the ketones, the phosphine oxides and the sulfoxides. Very particularly preferred host materials are selected from the classes of the oligoarylenes, comprising anthracene, benzanthracene and/or pyrene, or atropisomers of these compounds.

It is furthermore particularly preferred for the compounds of one of the formulae I, II, III or IV to be employed as hole-transport material and/or as hole-injection material. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which is located between the hole-injection layer and the emission layer. If the compounds of one of the formulae I, II, III or IV are used as hole-transport or hole-injection material, it may be preferred for them to be doped with electron-acceptor compounds, for example with $F_4$-TCNQ or with compounds as described in EP 1476881 or EP 1596445.

If the compound of one of the formulae I, II, III or IV is employed as hole-transport material in a hole-transport layer, a proportion of 100% may also be preferred, i.e. the use of this compound as pure material.

Particular preference is also given to the use of a compound of one of the formulae I, II, III or IV in a hole-transport or -injection layer in combination with a layer which comprises a hexaazatriphenylene derivative, in particular hexacyanohexaazatriphenylene (for example in accordance with EP 1175470). Thus, for example, preference is given to the following structure: anode-hexaazatriphenylene derivative-hole-transport layer, where the hole-transport layer comprises one or more compounds of the formula I, II, III or IV. It is likewise possible in this structure to use a plurality of successive hole-transport layers, where at least one hole-transport layer comprises at least one compound of the formula I, II, III or IV. The following structure is likewise preferred: anode-hole-transport layer-hexaazatriphenylene derivative-hole-transport layer, where at least one of the two hole-transport layers comprises one or more compounds of the formula I, II, III or IV. It is likewise possible in this structure to use a plurality of successive hole-transport layers instead of one hole-transport layer, where at least one hole-transport layer comprises at least one compound of the formula I, II, III or IV.

It is furthermore preferred for the compounds of one of the formulae I, II, III or IV to be employed as electron-transport material and/or as hole-blocking material for fluorescent and phosphorescent OLEDs and/or as triplet matrix material for phosphorescent OLEDs. This applies, in particular, to compounds in which the groups Y and X stand for C═O, P═O or S═O.

The invention furthermore relates to the use of the compounds defined above in electronic devices.

The compounds described above can also be used for the preparation of polymers, oligomers or dendrimers. This is usually carried out via polymerisable functional groups. To this end, particular preference is given to compounds which are substituted by reactive leaving groups, such as bromine, iodine, boronic acid, boronic acid ester, tosylate or triflate. These can also be used as comonomers for the generation of corresponding conjugated, partially conjugated or non-conjugated polymers, oligomers or also as the core of dendrimers. The polymerisation here is preferably carried out via the halogen functionality or the boronic acid functionality.

The invention thus furthermore relates to polymers, oligomers or dendrimers comprising one or more compounds of one of the formulae I, II, III or IV.

The bonds to the polymer, oligomer or dendrimer emanating from the compound of the formula I, II, III or IV can be localised at any desired position of the compounds which is characterised as optionally substituted by a radical R or $R^1$.

The polymers, oligomers or dendrimers may be conjugated, partially conjugated or non-conjugated. Likewise encompassed are blends of the polymers, oligomers or dendrimers according to the invention with further polymers, oligomers or dendrimers.

For the purposes of this invention, the term oligomer is applied to a compound which has about three to nine recurring units. For the purposes of the invention, a polymer is taken to mean a compound which has ten or more recurring units.

These polymers may comprise further recurring units. These further recurring units are preferably selected from the group consisting of fluorenes (for example in accordance with EP 842208 or WO 00/22026), spirobifluorenes (for example in accordance with EP 707020, EP 894107 or EP 04028865.6), triarylamines, para-phenylenes (for example in accordance with WO 92/18552), carbazoles (for example in accordance with WO 04/070772 and WO 04/113468), thiophenes (for example in accordance with EP 1028136), dihydrophenanthrenes (for example in accordance with WO 05/014689), indenofluorenes (for example in accordance with WO 04/041901 and WO 04/113412), aromatic ketones (for example in accordance with WO 05/040302), phenanthrenes (for example in accordance with WO 05/104264) and/or metal complexes, in particular ortho-metallated iridium complexes. It should expressly be pointed out here that the polymers may also have a plurality of different recurring units selected from one or more of the groups mentioned above.

The invention likewise relates to the use of the polymers, oligomers or dendrimers defined above in electronic devices.

The invention furthermore relates to an electronic device comprising at least one compound, as defined above, or a polymer, oligomer or dendrimer, as defined above.

The organic electronic device is preferably selected from the group consisting of organic electroluminescent devices (OLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors and organic laser diodes (O-lasers).

For the purposes of the invention, it is preferred for the compounds of one of the formulae I, II, III or IV according to the invention or the polymers, oligomers or dendrimers according to the invention to be employed as hole-transport material in a hole-transport layer and/or in a hole-injection layer in the organic electronic device and for it to be possible for the compounds of one of the formulae I, II, III or IV or the polymers, oligomers or dendrimers in these layers to be optionally doped with electron-acceptor compounds.

For the purposes of the invention, it is furthermore preferred for the compounds of one of the formulae I, II, III or IV according to the invention or the polymers, oligomers or dendrimers according to the invention to be employed as electron-transport material in an electron-transport layer and/or as hole-blocking material in a hole-blocking layer and/or as triplet matrix material in an emitting layer in the organic electroluminescent device.

It is furthermore preferred for the compounds of one of the formulae I, II, III or IV according to the invention or the polymers, oligomers or dendrimers according to the invention to be employed in an emission layer, preferably as emitting materials, in the electronic device.

The organic electroluminescent device comprises an anode, a cathode and at least one emitting layer, where the emitting layer or one of the other layers comprises at least one compound of one of the formulae I, II, III or IV or the polymers, oligomers or dendrimers according to the invention.

The cathode preferably comprises metals having a low work function, metal alloys or multilayered structures comprising different metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, where combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent in order to enable either the irradiation of the organic material (O-SCs) or the coupling-out of light (OLEDs/PLEDs, O-LASERS). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

The device is correspondingly (depending on the application) structured, provided with contacts and finally hermetically sealed, since the lifetime of such devices is drastically shortened in the presence of water and/or air.

Compounds of one of the formulae I, II, III or IV can also be employed either as emitting unit and/or as hole-transporting unit and/or as electron-transporting unit and/or as matrix unit in polymers, oligomers or dendrimers.

Preference is furthermore given to organic electroluminescent devices, characterised in that a plurality of emitting compounds are used in the same layer or in different layers. These compounds particularly preferably have in total a plurality of emission maxima between 380 nm and 750 nm, resulting overall in white emission, i.e. a plurality of emitting compounds which are able to fluoresce or phosphoresce are used. Particular preference is given to three-layer systems, where the layers exhibit blue, green and orange or red emission (for the basic structure see, for example, WO 05/011013). Broad-band emitters can likewise be used for white-emitting OLEDs.

Apart from the cathode, anode and emitting layer, the organic electroluminescent device may also comprise further layers. These can be, for example: hole-injection layer, hole-transport layer, hole-blocking layer, electron-transport layer, electron-blocking layer, electron-injection layer and/or charge-generation layer (T. Matsumoto et al., *Multiphoton Organic EL Device Having Charge Generation Layer*, IDMC 2003, Taiwan; Session 21 OLED (5)) or organic or inorganic pin junctions. Furthermore, interlayers may be introduced between the layers, in particular between two emitting layers. However, it should be pointed out at this point that each of these layers does not necessarily have to be present. Thus, in particular on use of compounds of one of the formulae I, II, III or IV with electron-conducting host materials, very good results are furthermore obtained if the organic electroluminescent device does not comprise a separate electron-transport layer and the emitting layer is directly adjacent to the electron-injection layer or to the cathode. Alternatively, the host material may also simultaneously serve as electron-transport material in an electron-transport layer. It may likewise be preferred for the organic electroluminescent device not to comprise a separate hole-transport layer and for the emitting layer to be directly adjacent to the hole-injection layer or to the anode. It may furthermore be preferred for the compound of one of the formulae I, II, III or IV simultaneously to be used as dopant in the emitting layer and as hole-conducting compound (as pure substance or as a mixture) in a hole-transport layer and/or in a hole-injection layer.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. However, it is also possible to work with an even lower pressure here, for example at an initial pressure of less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds of one of the formulae I, II, III or IV are necessary for this purpose. High solubility can be achieved through suitable substitution of the compounds. These processes for the production of layers are particularly suitable for polymers, oligomers or dendrimers.

The compounds according to the invention preferably have one or more of the following advantages over the prior art on use in organic electroluminescent devices:

1. The efficiency, in particular the power efficiency, of corresponding devices becomes higher compared with systems in accordance with the prior art.
2. The stability of corresponding devices becomes higher compared with systems in accordance with the prior art, which is evident, in particular, from a significantly longer lifetime. This applies, in particular, to the use of the compounds according to the invention in thick layers.
3. On use of the compounds according to the invention as hole-transport material in a hole-transport and/or hole-injection layer, it is found that the voltage is virtually independent of the layer thickness of the corresponding hole-transport or hole-injection layer. By contrast, a significant increase in voltage is obtained with materials in accordance with the prior art in the case of relatively thick layer thicknesses of the hole-transport or hole-injection layers, which in turn results in lower power efficiency of the OLED.
4. The materials according to the invention exhibit absolutely no or virtually no tendency to crystallise on the edge of the vapour-deposition source during the vapour-deposition process and to clog it. They are therefore more suitable for mass production than materials in accordance with the prior art which have this problem.

The present application text and also the examples below are directed to the use of the compounds according to the invention in relation to OLEDs and the corresponding displays. In spite of this restriction of the description, it is possible for the person skilled in the art, without further inventive step, also to employ the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors or also organic laser diodes (O-lasers), to mention but a few applications.

The present invention likewise relates to the use of the compounds according to the invention in the corresponding devices and to these devices themselves.

The invention is explained in greater detail by the following examples, without wishing to restrict it thereby.

EXAMPLES

The following syntheses are carried out, unless indicated otherwise, under a protective-gas atmosphere in dried solvents.

Example 1 a) Synthesis of the Thioether

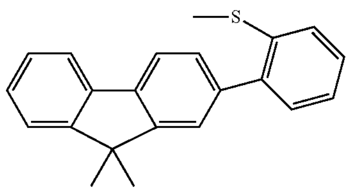 [SMILES: CSc1ccccc1-c1ccc2c(c1)C(C)(C)c1ccccc1-2]

200 g (732 mmol) of 2-bromo-9,9-dimethyl-9H-fluorene, 122.9 g (732 mmol) of 2-methylsulfanylphenylboronic acid and 202 g (950 mmol) of $K_2CO_3$ are suspended in 850 ml of THF and 850 ml of water, the mixture is saturated with $N_2$, 3.3 g (2.9 mmol) of tetrakis(triphenylphosphine)palladium (0) are added, and the mixture is heated at the boil for 2 h. The mixture is poured into 3 l of a mixture of water/MeOH/6 M HCl 1:1:1, and the beige precipitate is filtered off with suction, washed with water and dried. The content of product according to $^1$H-NMR is about 95% with an overall yield of 190 g (82%).

b) Oxidation

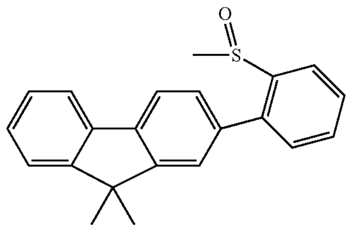 [SMILES: CS(=O)c1ccccc1-c1ccc2c(c1)C(C)(C)c1ccccc1-2]

196 g (619.3 mmol) of the compound from a) are initially introduced in 2.3 l of glacial acetic acid and 250 ml of dichloromethane under a protective gas and cooled to 0° C. 1.1 l (619 mmol) of 30% $H_2O_2$ solution are added dropwise to this solution, and the mixture is stirred overnight. $Na_2SO_3$ solution is added to the mixture, the phases are separated, and the solvent is removed in vacuo. The content of product according to $^1$H-NMR is about 98% with an overall yield of 200 g (99%).

c) Synthesis of the Indenodibenzothiophene

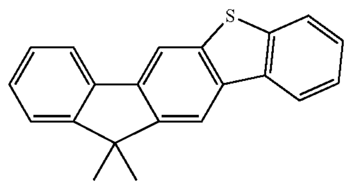 [SMILES: CC1(C)c2ccccc2-c2cc3sc4ccccc4c3cc21]

A mixture of 91 g (273 mmol) of the compound from b) and 737 ml (8329 mmol) of trifluoromethanesulfonic acid is stirred at 5° C. for 48 h. 2.4 l of water/pyridine 5:1 are subsequently added to the mixture, which is then heated under reflux for 20 min. After cooling to room temperature, 500 ml of water and 1000 ml of dichloromethane are carefully added. The organic phase is washed with 4×50 ml of $H_2O$, dried over $MgSO_4$, and the solvents are removed in vacuo. The pure product is obtained by recrystallisation. The content of product according to HPLC is 98% with an overall yield of 65 g (80%).

d) Bromination

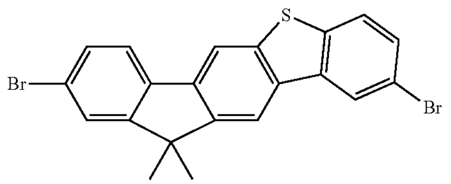 [SMILES: CC1(C)c2cc(Br)ccc2-c2cc3sc4ccc(Br)cc4c3cc21]

95.3 g (317.6 mmol) of the compound from c) are initially introduced in 2.5 l of dichloromethane under a protective gas and cooled to 5° C. 38.4 ml (763.2 mmol) of $Br_2$ dissolved in 250 ml of chloroform are added dropwise to this solution, and the mixture is stirred overnight. $Na_2SO_3$ solution is added to the mixture, the phases are separated, and the solvent is removed in vacuo. The content of product according to $^1$H-NMR is about 98% with an overall yield of 138 g (95%).

e) Synthesis of Amine-1

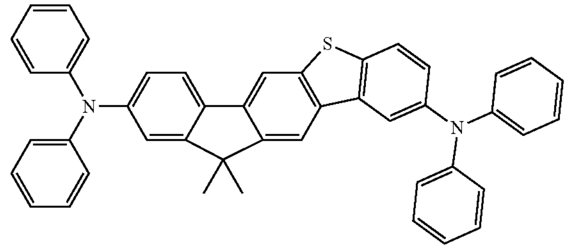 [SMILES: CC1(C)c2cc(N(c3ccccc3)c3ccccc3)ccc2-c2cc3sc4ccc(N(c5ccccc5)c5ccccc5)cc4c3cc21]

A degassed solution of 19.2 g (42 mmol) of the compound from d) and 26 g (93 mmol) of diphenylamine in 1000 ml of dioxane is saturated with $N_2$ for 1 h. Firstly 0.97 ml (4.2 mmol) of $P(^tBu)_3$, then 0.47 g (2.12 mmol) of palladium acetate are then added to the solution, and 12 g (127 mmol) of NaOtBu in the solid state are subsequently added. The reaction mixture is heated under reflux for 18 h. After cooling to room temperature, 1000 ml of water are carefully added. The organic phase is washed with 4×50 ml of $H_2O$, dried over $MgSO_4$, and the solvents are removed in vacuo. The pure product is obtained by recrystallisation. The content of product according to HPLC is 98% with an overall yield of 25 g (94%).

Examples 2-9

Production of OLEDs

OLEDs according to the invention are produced by a general process in accordance with WO 04/058911, which is adapted to the circumstances described here (layer-thickness variation, materials used).

The results for various OLEDs are presented in Examples 2 to 9 below. Glass plates coated with structured ITO (indium tin oxide) form the substrates of the OLEDs. For improved processing, 20 nm of PEDOT (poly-(3,4-ethylenedioxy-2,5-thiophene), applied by spin-coating from water, purchased from H. C. Starck, Goslar, Germany) are applied to the substrate. The OLEDs consist of the following layer sequence: substrate/PEDOT 20 nm/HIL1 5 nm/hole-transport layer (HTM) 20, 110 or 200 nm/NPB 20 nm/emission layer (EML) 30 or 40 nm/electron-transport layer (ETM) 20 nm and finally a cathode.

The materials apart from the PEDOT are applied by thermal vapour deposition in a vacuum chamber. The emission layer here always consists of a matrix material (host) and a dopant, which is admixed with the host by co-evaporation. In all the examples shown, the electron-transport layer consists of $Alq_3$ (aluminium trisquinolinate). The cathode is formed by an LIE layer with a thickness of 1 nm and an aluminium layer with a thickness of 100 nm deposited on top. Table 1 shows the chemical structures of the materials used to build up the OLEDs. HTM1, HTM2 and H2 here are materials in accordance with the prior art, amine-1 and H3 are examples of compounds according to the invention.

The OLEDs are characterised by standard methods. For this purpose, the electroluminescence spectra, the current efficiency (measured in cd/A), the power efficiency (measured in Im/W) as a function of the luminance, calculated from current-voltage-luminance characteristic lines (IUL characteristic lines), and the lifetime are determined. The lifetime is defined as the time after which the luminance has dropped to half from an initial value (25,000 cd/m$^2$ or 8000 cd/m$^2$). The use voltage is defined as the voltage at which the OLED achieves a luminance of 1 cd/m$^2$.

Table 2 shows the results for some OLEDs (Examples 2 to 9). The lifetimes are measured from an initial luminance of 25,000 cd/m$^2$ on use of fluorescent dopant D1 and from an initial luminance of 8000 cd/m$^2$ on use of phosphorescent dopant D2 ($Ir(ppy)_3$). The hole-transport material according to the invention used is compound amine-1, and the host material according to the invention used is compound H3 from Table 1. As comparison, compounds HTM1 and H2 respectively in accordance with the prior art are used.

Compared with the prior art, compound amine-1 is distinguished over compound HTM1 in accordance with the prior art on use as hole-transport material through a reduced use voltage and a reduced operating voltage (see Examples 2-7 in Table 2). This applies, in particular, on use of thick hole-transport layers, which are advantageous in mass production owing to the higher production yield (see Examples 4 and 7 in Table 2). Furthermore, slightly higher current efficiencies (measured in cd/A) arise on use of compound amine-1 according to the invention, which, together with the reduced voltage, results in significantly higher power efficiencies (measured in Im/W). The greatest improvement here is more than 30% on use of a hole-transport layer with a thickness of 200 nm (see Examples 4 and 7 in Table 2). This is an important aspect, in particular, for mobile applications, since the operating time here is crucially determined by the requisite power of the display. A further advantage of compound amine-1 according to the invention is that the lifetime breaks down to a much lesser extent in the case of relatively thick hole-transport layers compared with the prior art HTM1.

On use of compound H3 according to the invention as host material in a phosphorescent OLED, a number of advantages arise compared with the use of compound H2 in accordance with the prior art (see Examples 8 and 9 in Table 2). Firstly, a significant reduction in the use and operating voltage arises, but, in particular, significantly improved current efficiency is obtained on use of compound H3 according to the invention, which enables a great increase in the power efficiency by a factor of about two to be achieved compared with the prior art. Furthermore, a lifetime which is longer by a factor of about 3.5 is obtained compared with OLEDs in which compound H2 in accordance with the prior art is used.

TABLE 1

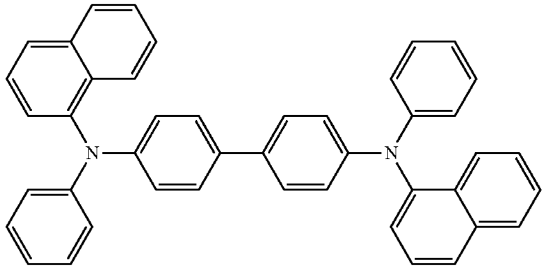

NPB

TABLE 1-continued
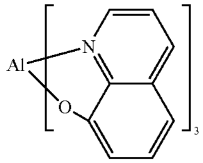
$AlQ_3$
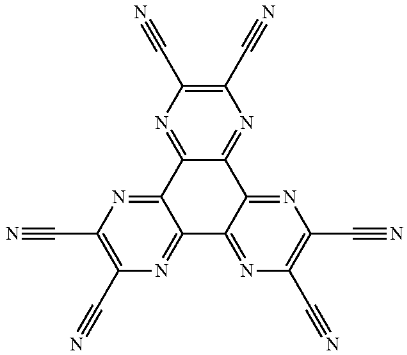
HIL1
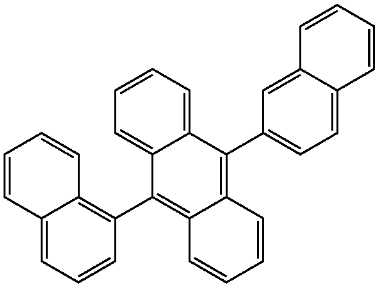
H1
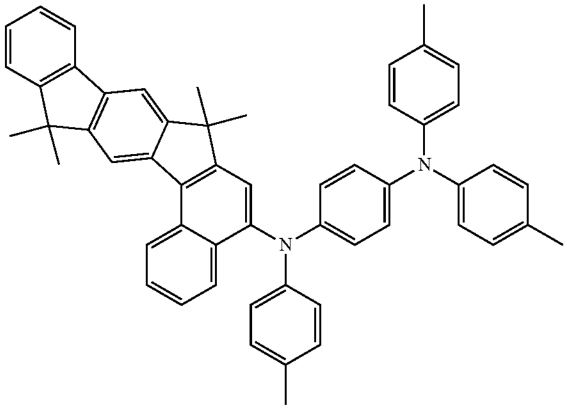
D1
TABLE 1-continued
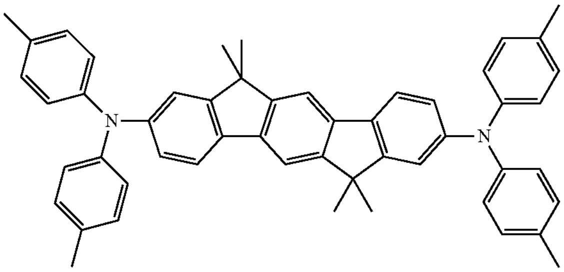
HTM1
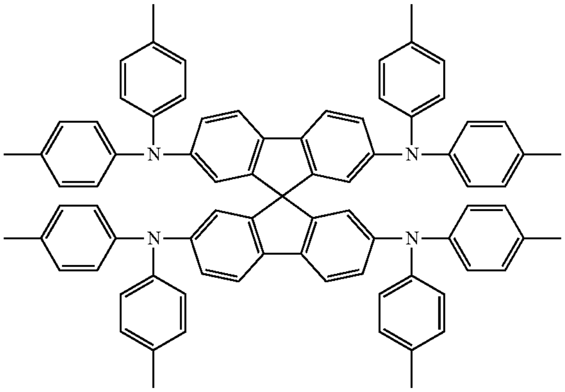
HTM2
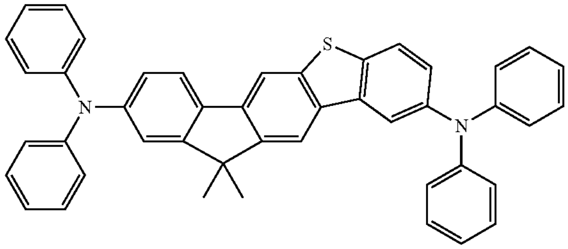
Amine-1 (according to Ex. 1)
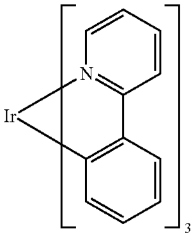
D2

TABLE 1-continued

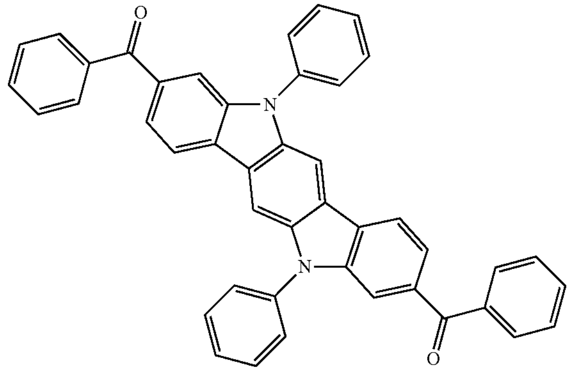

H2

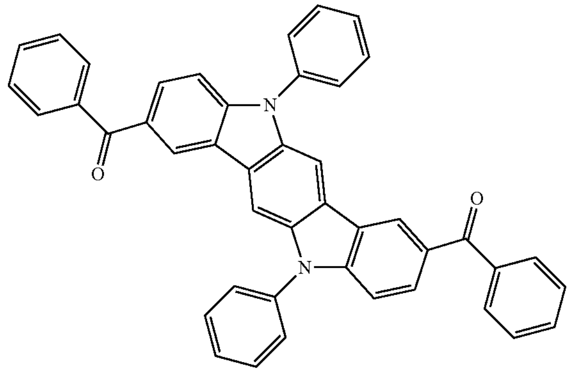

H3

The invention claimed is:

1. A compound of general formula VI, formula VI

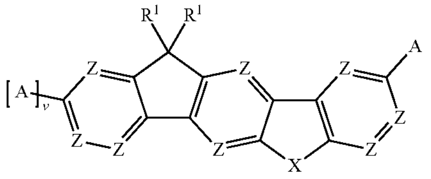

wherein

A corresponds to general formula V formula V

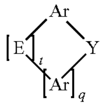

and wherein the link to the compound of the general formula VI takes place via Y;

Y is N;

Z is in each case, independently of one another, CR;

X is S;

R is H;

$R^1$ is in each case, independently of one another, H, D or unsubstituted $C_1$-$C_5$alkyl group;

Ar is in each case, independently of one another, is phenyl or biphenyl which is optionally substituted by one or more radicals $R^1$;

E is not present;

q=1;

t is 0 which means that two group $R^1$ are bonded instead of E;

v is 1.

TABLE 2

| Ex. | EML thickness | HTM thickness | Use voltage | Voltage for 1000 cd/m$^2$ | Efficiency at 1000 cd/m$^2$ | Efficiency at 1000 cd/m$^2$ | CIE x/y at 1000 cd/m$^2$ | |
|---|---|---|---|---|---|---|---|---|
| | | | | | | | | Lifetime from 25,000 cd/m$^2$ |
| 2 comp. | H1 + 10% of D1 30 nm | HTM 1 20 nm | 3.2 V | 5.2 V | 14.8 cd/A | 8.9 lm/W | 0.31/0.58 | 350 h |
| 3 comp. | H1 + 10% of D1 30 nm | HTM 1 110 nm | 3.1 V | 5.5 V | 17.1 cd/A | 9.7 lm/W | 0.29/0.61 | 243 h |
| 4 comp. | H1 + 10% of D1 30 nm | HTM 1 200 nm | 4.1 V | 6.9 V | 15.0 cd/A | 6.8 lm/W | 0.30/0.58 | 171 h |
| 5 | H1 + 10% of D1 30 nm | Ex. amine-1 20 nm | 2.7 V | 4.9 V | 16.2 cd/A | 10.4 lm/W | 0.30/0.59 | 346 h |
| 6 | H1 + 10% of D1 30 nm | Ex. amine-1 110 nm | 2.8 V | 5.1 V | 18.3 cd/A | 11.3 lm/W | 0.29/0.61 | 281 h |
| 7 | H1 + 10% of D1 30 nm | Ex. amine-1 200 nm | 2.8 V | 5.6 V | 16.1 cd/A | 9.0 lm/W | 0.30/0.57 | 287 h |
| | | | | | | | | Lifetime from 8000 cd/m$^2$ |
| 8 comp. | H2 + 15% of D2 40 nm | HTM 2 20 nm | 2.4 V | 5.2 V | 17.2 cd/A | 10.4 lm/W | 0.38/0.56 | 39 h |
| 9 | Ex. H3 + 15% of D2 40 nm | HTM 2 20 nm | 2.2 V | 4.4 V | 30.0 cd/A | 21.4 lm/W | 0.39/0.58 | 135 h |

2. The compound of claim 1, where Ar is phenyl.

3. A polymer, oligomer or dendrimer comprising at least one compound of claim 1, where the bonds to the polymer, oligomer, or dendrimer emanating from the compound according to claim 1 can be localised at any position of the compound which is characterised as optionally substituted by a radical R or $R^1$.

4. An electronic device comprising at least one compound of claim 1.

5. The electronic device of claim 4, wherein said electronic device is selected from the group consisting of organic electroluminescent devices, organic field-effect transistors, organic thin-film transistors, organic light-emitting transistors, organic integrated circuits, organic solar cells, organic field-quench devices, light-emitting electrochemical cells, organic photoreceptors, and organic laser diodes.

6. An organic electroluminescent device, wherein said at least one compound of claim 1 is employed as hole-transport material in a hole-transport layer and/or in a hole-injection layer, wherein said at least one compound in these layers are optionally doped with electron-acceptor compounds, and/or wherein said at least one compound of claim 1 is employed as electron-transport material in an electron-transport layer and/or as hole-blocking material in a hole-blocking layer and/or as triplet matrix material in an emitting layer and/or in that the emitting layer of said organic electroluminescent device comprises at least one compound of claim 1.

7. A process for preparing the compound of claim 1, comprising a) carrying out a metal-catalysed cross-coupling reaction of an $X^1$-substituted aromatic or heteroaromatic dihalogen compound with further aromatic or heteroaromatic compounds, which are optionally substituted by A, to form a coupled aromatic or heteroaromatic compound;

b) forming a divalent bridge —X— between said coupled aromatic or heteroaromatic compound;

wherein $X^1$ is a radical which can be converted into X.

8. An electronic device comprising at least one polymer, oligomer, or dendrimer of claim 3.

9. An organic electroluminescent device, wherein said at least one polymer, oligomer, or dendrimer of claim 3 is employed as hole-transport material in a hole-transport layer and/or in a hole-injection layer, wherein said at least one polymer, oligomer or dendrimer in these layers are optionally doped with electron-acceptor compounds, and/or wherein said at least one polymer, oligomer or dendrimer of claim 3 is employed as electron-transport material in an electron-transport layer and/or as hole-blocking material in a hole-blocking layer and/or as triplet matrix material in an emitting layer and/or in that the emitting layer of said organic electroluminescent device comprises at least one polymer, oligomer or dendrimer of claim 3.

* * * * *